(12) United States Patent
Gazit

(10) Patent No.: US 8,563,273 B2
(45) Date of Patent: Oct. 22, 2013

(54) METHOD OF SCREENING FOR COMPOUNDS THAT DISAGGREGATE AMYLOID AGGREGATES

(75) Inventor: Ehud Gazit, Ramat-HaSharon (IL)

(73) Assignee: Tel Aviv University Future Technology Development L.P., Tel-Aviv (IL)

( * ) Notice: Subject to any disclaimer, the term of this patent is extended or adjusted under 35 U.S.C. 154(b) by 576 days.

(21) Appl. No.: 12/385,471

(22) Filed: Apr. 9, 2009

(65) Prior Publication Data

US 2009/0209041 A1 Aug. 20, 2009

Related U.S. Application Data

(60) Division of application No. 11/656,542, filed on Jan. 23, 2007, now abandoned, which is a continuation of application No. 10/235,852, filed on Sep. 6, 2002, now abandoned.

(51) Int. Cl.
*C12P 19/42* (2006.01)
*A61K 38/04* (2006.01)

(52) U.S. Cl.
USPC .............. 435/86; 530/327; 530/328; 530/329

(58) Field of Classification Search
None
See application file for complete search history.

(56) References Cited

U.S. PATENT DOCUMENTS

| | | | |
|---|---|---|---|
| 3,791,932 | A | 2/1974 | Schuurs et al. |
| 3,839,153 | A | 10/1974 | Schuurs et al. |
| 3,850,578 | A | 11/1974 | McConnell |
| 3,850,752 | A | 11/1974 | Schuurs et al. |
| 3,853,987 | A | 12/1974 | Dreyer |
| 3,867,517 | A | 2/1975 | Ling |
| 3,879,262 | A | 4/1975 | Schuurs et al. |
| 3,901,654 | A | 8/1975 | Gross |
| 3,935,074 | A | 1/1976 | Rubenstein et al. |
| 3,984,533 | A | 10/1976 | Uzgiris |
| 3,996,345 | A | 12/1976 | Ullman et al. |
| 4,034,074 | A | 7/1977 | Miles |
| 4,098,876 | A | 7/1978 | Piasio et al. |
| 4,626,540 | A | 12/1986 | Capps et al. |
| 4,666,828 | A | 5/1987 | Gusella |
| 4,683,202 | A | 7/1987 | Mullis |
| 4,801,531 | A | 1/1989 | Frossard |
| 4,873,316 | A | 10/1989 | Meade et al. |
| 4,879,219 | A | 11/1989 | Wands et al. |
| 4,970,233 | A | 11/1990 | McHugh |
| 5,011,771 | A | 4/1991 | Bellet et al. |
| 5,192,659 | A | 3/1993 | Simons |
| 5,272,057 | A | 12/1993 | Smulson et al. |
| 5,281,521 | A | 1/1994 | Trojanowski et al. |
| 5,556,744 | A | 9/1996 | Weiner et al. |
| 5,593,967 | A | 1/1997 | Horwell et al. |
| 5,659,041 | A | 8/1997 | Pollak et al. |
| 5,688,561 | A | 11/1997 | Ichikawa et al. |
| 6,261,569 | B1 | 7/2001 | Comis et al. |
| 6,303,567 | B1 | 10/2001 | Findeis et al. |
| 6,359,112 | B2 | 3/2002 | Kapurniotu et al. |
| 6,593,339 | B1 | 7/2003 | Eek et al. |
| 6,610,478 | B1 | 8/2003 | Takle et al. |
| 6,617,114 | B1 | 9/2003 | Fowlkes et al. |
| 6,677,153 | B2 | 1/2004 | Iversen |
| 6,689,753 | B1 | 2/2004 | Soto-Jara |
| 7,732,479 | B2 | 6/2010 | Gazit et al. |
| 7,781,396 | B2 | 8/2010 | Gazit |
| 8,012,929 | B2 | 9/2011 | Gazit |
| 2001/0007015 | A1 | 7/2001 | Kapurniotu et al. |
| 2001/0012889 | A1 | 8/2001 | LaFleur et al. |
| 2002/0035061 | A1 | 3/2002 | Krieger et al. |
| 2003/0130484 | A1 | 7/2003 | Gordon et al. |
| 2003/0225155 | A1 | 12/2003 | Fernandez-Pol et al. |
| 2004/0052928 | A1 | 3/2004 | Gazit |
| 2005/0020809 | A1 | 1/2005 | Gazit |
| 2006/0234947 | A1 | 10/2006 | Gazit |
| 2007/0021345 | A1 | 1/2007 | Gazit |
| 2007/0135334 | A1 | 6/2007 | Gazit |
| 2007/0138007 | A1 | 6/2007 | Yemini et al. |
| 2009/0156471 | A1 | 6/2009 | Gazit et al. |
| 2010/0022459 | A1 | 1/2010 | Gazit |

FOREIGN PATENT DOCUMENTS

| | | |
|---|---|---|
| AU | 2003207973 | 9/2003 |
| AU | 2004203461 | 11/2004 |
| DE | 3412445 | 10/1985 |
| DE | 10043282 | 3/2002 |
| EP | 0081122 | 6/1983 |
| EP | 0264166 | 4/1988 |
| EP | 0421946 | 4/1991 |
| EP | 0885904 | 6/1998 |
| FR | 1373316 | 9/1964 |
| JP | 59-044313 | 3/1984 |
| JP | 60-040061 | 3/1985 |
| JP | 63-044895 | 2/1988 |
| JP | 02-295923 | 12/1990 |
| JP | 11-514333 | 12/1999 |

(Continued)

OTHER PUBLICATIONS

Requisition by the Examiner Dated Aug. 3, 2010 From the Canadian Intellectual Property Office Re. Application No. 2,473,987.
Official Action Dated Jun. 14, 2010 From the US Patent and Trademark Office Re.: U.S. Appl. No. 12/458,163.
Examination Report Dated Jan. 8, 2008 From the Government of India, Patent Office Re.: Application No. 1671/CHENP/2004.
Examination Report Dated Jun. 19, 2007 of the Government of India, Patent Office Re.: Application No. 1671/CHENP/2004.
Examiner's Report Dated Feb. 17, 2009 From the Australian Government, IP Australia Re.: Application No. 2004203461.
Examiner's Report Dated Feb. 22, 2008 From the Australian Government, IP Australia Re.: Application No. 2004203461.
Examiner's Report Dated Jun. 22, 2009 From the Australian Government, IP Australia Re.: Application No. 2004203461.
International Preliminary Report on Patentability Dated Jan. 22, 2009 From the International Bureau of WIPO Re.: Application No. PCT/IL2004/000577.

(Continued)

*Primary Examiner* — Christian Fronda

(57) ABSTRACT

A peptide comprising at least 5 amino acid residues and less than 15 amino acid residues, the peptide including an amino acid sequence as set forth in SEQ ID NO: 7 as well as pharmaceutical compositions, kits and methods for diagnosing and treating amyloid associated diseases.

7 Claims, 6 Drawing Sheets

(56) References Cited

FOREIGN PATENT DOCUMENTS

| JP | 2000-193661 | 7/2000 |
|---|---|---|
| JP | 2001-500852 | 1/2001 |
| JP | 2001-504334 | 4/2001 |
| WO | WO 80/00789 | 1/1980 |
| WO | WO 92/19253 | 11/1992 |
| WO | WO 95/08999 | 4/1995 |
| WO | WO 96/28471 | 9/1996 |
| WO | WO 96/39834 | 12/1996 |
| WO | WO 97/16191 | 5/1997 |
| WO | WO 98/08868 | 3/1998 |
| WO | WO 98/20135 | 5/1998 |
| WO | WO 99/27944 | 6/1999 |
| WO | WO 01/10457 | 2/2001 |
| WO | WO 01/21188 | 3/2001 |
| WO | WO 01/34631 | 5/2001 |
| WO | WO 01/45726 | 6/2001 |
| WO | WO 01/93836 | 12/2001 |
| WO | WO 03/063760 | 8/2003 |
| WO | WO 03/077866 | 9/2003 |
| WO | WO 03/077869 | 9/2003 |
| WO | WO 2006/006172 | 1/2006 |
| WO | WO 2007/043046 | 4/2007 |
| WO | WO 2009/000634 | 12/2008 |
| WO | WO 2009/095265 | 8/2009 |
| WO | WO 2012/066549 | 5/2012 |

OTHER PUBLICATIONS

International Preliminary Report on Patentability Dated Jan. 25, 2007 From the International Bureau of WIPO Re.: Application No. PCT/IL2005/000754.
International Search Report Dated Jul. 19, 2004 From the International Searching Authority Re.: Application No. PCT/IL03/01045.
Office Action Dated Feb. 1, 2009 From the Israeli Patent Office Re.: Application No. 163285 and Its Translation Into English.
Office Action Dated Jun. 4, 2008 From the Israeli Patent Office Re.: Application No. 163285.
Office Action Dated Nov. 5, 2009 From the Israel Patent Office Re. Application No. 172788 and Its Translation Into English.
Office Action Dated Jan. 8, 2009 From the Israeli Patent Office Re.: Application No. 172788 and Its Translation Into English.
Official Action Dated May 2, 2008 From the US Patent and Trademark Office Re.: U.S. Appl. No. 11/656,542.
Official Action Dated Sep. 2, 2008 From the US Patent and Trademark Office Re.: U.S. Appl. No. 11/471,657.
Official Action Dated Jul. 5, 2007 From the US Patent and Trademark Office Re.: U.S. Appl. No. 11/471,657.
Official Action Dated Sep. 10, 2007 From the US Patent and Trademark Office Re.: U.S. Appl. No. 11/471,657.
Official Action Dated Dec. 12, 2008 From the US Patent and Trademark Office Re.: U.S. Appl. No. 11/656,542.
Official Action Dated May 15, 2009 From the US Patent and Trademark Office Re.: U.S. Appl. No. 11/471,657.
Official Action Dated Dec. 16, 2008 From the US Patent and Trademark Office Re.: U.S. Appl. No. 10/562,852.
Official Action Dated Apr. 19, 2006 From the US Patent and Trademark Office Re.: U.S. Appl. No. 10/901,243.
Official Action Dated Aug. 21, 2009 From the US Patent and Trademark Office Re.: U.S. Appl. No. 10/562,852.
Official Action Dated Feb. 23, 2006 From the US Patent and Trademark Office Re.: U.S. Appl. No. 10/235,852.
Response Dated Nov. 2, 2009 to Reason for Rejection of Aug. 11, 2009 From the Japanese Patent Office Re.: Application No. 2003-563456.
Search Results: STN File, Registry, RN 379722-40-4 and Following Dated Dec. 31, 2001 for the Australian Patent Application No. 2004203461.
Supplementary European Search Report Dated Apr. 18, 2006 From the European Patent Office Re.: Application No. 03704977.2.
Translation of Reason for Rejection Dated Aug. 11, 2009 From the Japanese Patent Office Re.: Application No. 2003-563456.
Translation of the Notice of Reason of Rejection Dated Jul. 11, 2008 From the Japanese Patent Office Re.: Application No. 2003-563456.
Written Opinion Dated Jun. 15, 2006 From the International Preliminary Examining Authority Re.: Application No. PCT/IL03/00079.
Anguiano et al. "Protofibrillar Islet Amyloid Polypeptide Permeabilizes Synthetic Vesicles by a Pore-Like Mechanism That May Be Relevant to Type II Diabetes", Biochemistry, 41: 11338-11343, 2002.
Arvinte et al. "The Structure and Mechanism of Formation of Human Calcitonin Fibrils", The Journal of Biological Chemistry, 268(9): 6415-6422, 1993.
Austin et al. "Medical Progress: Calcitonin. Physiology and Pathophysiology", The New England Journal of Medicine, 304(5): 269-278, 1981.
Ausubel et al. Current Protocols in Molecular Biology, 1(Suppl.63).
Azriel et al. "Analysis of the Minimal Amyloid-Forming Fragment of the Islet Amyloid Polypeptide", The Journal of Biological Chemistry, 276(36): 34156-34161, 2001.
Balbach et al. "Supramolecular Structure in Full-Length Alzheimer's β-Amyloid Fibrils: Evidence for a Parallel β-Sheet Organization From Solid-State Nuclear Magnetic Resonance", Biophysical Journal, 83: 1205-1216, 2002.
Baltzer et al. "De Novo Design of Proteins—What Are the Rules?", Chemical Reviews, 101(10): 3153-3163, 2001.
Banerji et al. "A Lymphocyte-Specific Cellular Enhancer Is Located Downstream of the Joining Region in Immunoglobulin Heavy Chain Genes", Cell, 33: 729-740, 1983.
Bauer et al. "Interfacial Adsorption and Aggregation Associated Changes in Secondary Structure of Human Calcitonin Monitored by ATR-FTIR Spectroscopy", Biochemistry, 33: 12276-12282, 1994.
Benvenga et al. "Homology of Calcitonin With the Amyloid-Related Proteins", Journal of Endocrinological Investigation, 17: 119-122, 1994.
Berger et al. "Calcitonin-Like Immunoreactivity of Amyloid Fibrils in Medullary Thyroid Carcinomas", Virchows Archiv A Pathological Anatomy and Histopathology, 412: 543-551, 1988.
Bird et al. "Single-Chain Antigen-Binding Proteins", Science, 242(4877): 423-426, 1988.
Boerner et al. "Production of Antigen-Specific Human Monoclonal Antibodies From In Vitro-Primed Human Splenocytes", The Journal of Immunology, 147(1): 86-95, 1991.
Bong et al. "Self-Assembling Organic Nanotubes", Angewandte Chemie, International Edition, 40:988-1011, 2001.
Booth et al. "Instability, Unfolding and Aggregation of Human Lysozyme Variants Underlying Amyloid Fibrillogenesis", Nature, 385: 787-793, 1997.
Bursavich et al. "Designing Non-Peptide Peptidomimetics in the 21st Century: Inhibitors Targeting Comformational Ensembles", Journal of Medical Chemistry, 45(3): 541-558, 2002.
Byrne et al. "Mutiplex Gene Regulation: A Two-Tiered Approach to Transgene Regulation in Transgenic Mice", Proc. Natl. Acad. Sci. USA, 86: 5473-5477, 1989.
Calame et al. "Transcriptional Controlling Elements in the Immunoglobulin and T Cell Receptor Loci", Advances in Immunology, 43: 235-275, 1988.
Cherny et al. "The Formation of *Escherichia coli* Curli Amyloid Fibrils is Mediated by Prion-Like Peptide Repeats", Journal of Molecular Biology, 352(2): 245-252, 2005.
Choplin "Computers and the Medicinal Chemist", Comprehensive Medicinal Chemistry, 4(Chap.17.2): 33-58, 1990.
Chou et al. "Conformational Parameters for Amino Acids in Helical, β-Sheet, and Random Coil Regions Calculated From Proteins", Biochemistry, 13(2): 211-222, 1974.
Claessens et al. "Review Commentary: π-π Interactions in Self-Assembly", Journal of Physical Organic Chemistry, 10: 254-272, 1997.
Cole et al. "Human Monoclonal Antibodies", Molecular &. Cellular Biochemistry, 62(2): 109-120, 1984.
Cole et al. "The EBV-Hybridoma Technique and Its Application to Human Lung Cancer", Monoclonal Antibodies and Cancer Therapy, Proceedings of the Roche-UCLA Symposium, Park City, Utah, p. 77-96, 1985.

(56) References Cited

OTHER PUBLICATIONS

Cooper "Selective Amyloid Staining as a Function of Amyloid Composition and Structure. Histochemical Analysis of the Alkaline Congo Red. Standardized Toluidine Blue, and Iodine Methods", Laboratory Investigation, 31(3): 232-238, 1974.
Copp "Endocrine Regulation of Calcium Metabolism", Annual Reviews in Physiology, 32: 61-86, 1970.
Cote et al. "Generation of Human Monoclonal Antibodies Reactive With Cellular Antigens", Proc. Natl. Acad. Sci. USA, 80: 2026-2030, 1983.
Coughlan et al. "Factors Influencing the Processing and Function of the Amyloid Beta Precursor Protein—A Potential Therapeutic Target in Alzheimer's Disease?", Pharmacology and Therapeutics, 86: 111-144, 2000.
Damas et al. "Review: TTR Amyloidosis—Structural Features Leading to Protein Aggregation and Their Implications on Therapeutic Strategies", Journal of Structural Biology, 130: 290-299, 2000.
Edlund et al. "Cell-Specific Expression of the Rat Insuline Gene: Evidence for Role of Two Distinct 5' Flanking Elements", Science, 230(4278): 912-916, 1985.
Ferrannini "Insulin Resistance Versus Insulin Deficiency in Non-Insulin-Dependent Diabetes Mellitus: Problems and Prospects", Endocrine Reviews, 19(4): 477-490, 1998.
Findeis "Approaches to Discovery and Characterization of Inhibitors of Amyloid Beta-Peptide Polymerization", Biochimica et Biophysica Acta, 1502: 76-84, 2000.
Findeis et al. "Modified-Peptide Inhibitors of Amyloid β-Peptide Polymerization", Biochemistry, 38: 6791-6800, 1999.
Fishwild et al. "High-Avidity Hum IgGκ Monoclonal Antibodies From a Novel Strain of Minilocus Transgenic Mice", Nature Biotechnology, 14: 845-851, 1996.
Forloni et al. "Anti-Amyloidogenic Activity of Tetracyclines: Studies in Vitro", FEBS Letters, 487(3): 404-407, 2001. Figs. 1,3.
Freshney "Animal Cell Culture—A Practical Approach", IRL Press.
Friedman "Chemistry, Nutrition, and Microbiology of D-Amino Acids", Journal of Agriculture and Food Chemistry, 47(9): 3457-3479, 1999.
Gait "Oligonucleotide Synthesis—A Practical Approach", IRL Press.
Gajdusek "Unconventional Viruses and the Origin and Disappearance of Kuru", Science, 197(4307): 943-960, 1977.
Gazit "A Possible Role for 'Phi'-Stacking in the Self-Assembly of Amyloid Fibrils", The FASEB Journal, 16: 77-83, 2002.
Gazit "Global Analysis of Tandem Aromatic Optapeptide Repeats: The Significance of the Aroma-Glycine Motif", Bioinformatics Discovery Note, 18(6): 880-883, 2002.
Gazit "The 'Correctly Folded' State of Proteins: Is It a Metastable State?", Angewandte Chemie, International Edition, 41(2): 257-259, 2002.
Gillard et al. "Controlling Self-Assembly", Chemical European Journal, 3(12): 1933-1940, 1997.
Gillmore et al. "Amyloidosis A Review of Recent Diagnostic and Therapeutic Developments", British Journal of Haematology, 99: 245-256, 1997.
Glenner "Amyloid Deposits and Amyloidosis. The Beta-Fibrilloses (First of Two Parts)", The New England Journal of Medicine, 302(23): 1283-1292, 1980.
Gorman et al. "Alzheimer Beta-Amyloid Peptides, Structures of Amyloid Fibrils and Alternate Aggregation Products", Biopolymers, 60: 381-394, 2001. Claims 1-16, 22-26, 70-80, 91-100.
Grateau "Le Curli du Coli: Une Variété Physiologique d'Amilose [Coli's Curli or How Amyloid Can be Physiological]", Médecine Sciences, 18(6-7): p. 664, 2002.
Häggqvist et al. "Medin: An Integral Fragment of Aortic Smooth Muscle Cell-Produced Lactadherin Forms the Most Common Human Amyloid", Proc. Natl. Acad. Sci. USA, 96: 8669-8674, 1999.
Han et al. "Technetium Complexes for the Quantitation of Brain Amyloid", Journal of the American Chemical Society, 118: 4506-4507, 1996.

Harlow et al. "Antibodies: A Laboratory Manual", Cold Spring Harbor Laboratory, p. III-IX, 1988.
Harrison et al. "Amyloid Peptides and Proteins in Review", Reviews in Physiology, Biochemistry and Pharmacology, 159: 1-77, 2007.
Hayden et al. "'A' Is for Amylin and Amyloid in Type 2 Diabetes Mellitus", JOP Journal of the Pancreas (Online), 2(4): 124-139, 2001.
Hoogenboom et al. "By-Passing Immunisation. Human Antibodies From Synthetic Repertoires of Germline $V_H$ Gene Segments Rearranged In Vitro", Journal of Molecular Biology, 227: 381-388, 1992.
Höppener et al. "Islet Amyloid and Type 2 Diabetes Mellitus", The New England Journal of Medicine, 343(6): 411-419, 2000.
Inbar et al. "Localization of Antibody-Combining Sites Within the Variable Portions of Heavy and Light Chains", Proc. Natl. Acad. Sci. USA, 69(9): 2659-2662, 1972.
Inglot "Comparison of the Antiviral Activity In Vitro of Some Non-Steroidal Anti-Inflammatory Drugs", Journal of General Virology, 4(2): 203-214, 1969.
Inouye et al "Synthesis and Biological Properties of the 10-Substituted Analogues of ACTH-(1-18)-NH2", Shionogi Research Laboratory, Fukushima-Ku, Osaka, p. 177-182, 1978.
Jelokhani-Niaraki et al "Changes in Conformation and Antimicrobial Properties Caused by Replacement of D-Amino Acids With α-Aminoisobutyric Acid in the Gramicidin Backbbone: Synthesis and Circular Dichroic Studies", Journal of the Chemical Society Perkin Transactions, 2: 1 187-1193, 1992.
Johnson et al. "Islet Amyloid, Islet-Amiloid Polypeptide, and Diabetes Mellitus", The New England Journal of Medicine, 321(8): 513-518, 1989.
Jones et al. "Replacing the Complementarity-Determining Regions in a Human Antibody With Those From a Mouse", Nature, 321: 522-525, 1986.
Kahn et al. "Islet Amyloid: A Long-Recognized but Underappreciated Pathological Feature of Type 2 Diabetes", Diabetes, 48: 241-253, 1999.
Kamihira et al. "Conformational Transitions and Fibrillation Mechanism of Human Calcitonin as Studied by High-Resolution Solid-State 13C NMR [in Process Citation]", Protein Science, 9: 867-877, 2000.
Kanaori et al. "Study of human Calcitonin Fibrillation by Proton Nuclear Magnetic Resonance Spectroscopy", Biochemistry, 34: 12138-12143, 1995.
Kapurniotu et al. "Structure-Based Design and Study of Non-Amyloidogenic, Double N-Methylated IAPP Amyloid Core Sequences as Inhibitors of IAPP Amyloid Formation and Cytotoxicity", Journal of Molecular Biology, 315: 339-350, 2002.
Kapurniotu et al. Database, Accession No. AAW93015, 1991.
Karle et al. "Structural Characteristics of α-Helical Peptide Molecules Contianing Aib Residues", Biochemistry, 29(29): 6747-6756, Jul. 24, 1990.
Kedar et al. "In Vitro Synthesis of 'Amyloid' Fibrils From Insulin, Calcitonin and Parathormone", Israel Journal of Medical Science, 12(10): 1137-1140, 1976.
Kilkarni et al. "Investigation of the Effect of Antisense Oligodeoxynucleotides to Islet Amyloid Polypeptide mRNA on Insulin Release, Content and Expression", Journal of Endocrinology, 151: 341-348, 1996.
Kohler et al. "Continuous Cultures of Fused Cells Secreting Antibody of Predefined Specifity", Nature, 256: 495-497. 1975.
Kozbor et al. "Specific Immunoglobulin Production and Enhanced Tumorigenicity Following Ascites Growth of Human Hybridomas", Journal of Immunological Methods, 81: 31-42, 1985.
Kuner et al. "Controlling Polmerization of Beta-Amyloid and Prion-Derived Peptides With Synthetic Smal Molecule Ligands", Journal of Biological Chemistry, 275(3): 1673-1678, 2000.
Kyte et al. "A Simple Method for Displaying the Hydropathic Character of a Protein", Journal of Molecular Biology, 157: 105-132, 1982.
Lansbury "Following Nature's Anti-Amyloid Strategy", Nature Biotechnology, 19(2): 112-113, 2001. p. 112, Left-Hand col., Paragraph 1-Middle col., Paragraph 1.
Larrick et al. "PCR Amplification of Antibody Genes", Methods: A Companion to Methods in Enzymology, 2(2): 106-110, 1991.

(56) References Cited

OTHER PUBLICATIONS

Lonberg et al. "Antigen-Specific Human Antibodies From Mice Comprising Four Distinct Genetic Modifications", Nature, 368(6474): 856-859, 1994.
Lonberg et al. "Human Antibodies From Transgenic Mice", International Review of Immunology, 13: 65-93, 1995.
Lowe et al. "Structure-Function Relationships for Inhibitors of β-Amyloid Toxicity Containing the Recognition Sequence KLVFF", Biochemistry, 40: 7882-7889, 2001.
Lyon et al. "Self-Assembly and Gelation of Oxidized Gluthathione in Organic Solvents", Journal of the American Chemical Society, 123: 4408-4413, 2001.
Marks et al. "By-Passing Immunization—Human Antibodies From V-Gene Libraries Displayed on Phage", Journal of Molecular Biology, 222: 581-597, 1991.
Marks et al. "By-Passing Immunization: Building High Affinity Human Antibodies by Chain Shuffling", Bio/Technology, 10: 779-783, 1992.
Marshak et al. "Strategies for Protein Purification and Charcterization, A Laboratory Course Manual", Cold Spring Harbor Laboratory Press, 1996.
Maury et al. "Creation of Amyloid Fibrils From Mutant ASN187 Gelsolin Peptides", Biochemical and Biophysical Research Communications, 183(1): 227-231, 1992.
Mazor et al. "Identification and Characterization of a Novel Molecular-Recognition and Self-Assembly Domain Within the Islet Amyloid Polypeptide", Journal of Molecular Biology, 322: 1013-1024, 2002.
McGaughey et al. "π-Stacking Interactions", The Journal of Biological Chemistry, 273(25): 15458-15463, 1998.
Medore et al. "Fatal Familial Insomnia, A Prion Disease With a Mutation at Codon 178 of the Prion Protein Gene", The New England Journal of Medicine, 326(7): 444-449, 1992.
Merlini et al. "Intereaction of the Anthracycline 4'-Iodo-4'-Deoxydoxorubicin With Amyloid Fibrils: Inhibition of Amyloidogenesis", Proc. Natl. Acad. Sci. USA, 92: 2959-2963, 1995.
Moriatry et al. "Effects of Sequential Proline Substitutions on Amoyloid Formation by Human Amylin20-29", Biochemistry, 38: 1811-1818, 1999.
Morrison "Success in Specification", Nature, 368(6474): 812-813, 1994.
Mosmann "Rapid Colorimetric Assay for Cellular Growth and Survival: Application to Proliferation and Cytotoxicity Assays", Journal of Immunological Methods, 65: 55-63, 1983.
Mosselman et al. "Islet Amyloid Polipeptide: Identification and Chromosomal Localization of the Human Gene", FEBS Letters, 239(2): 227-232, 1988.
Mutter "Studies on the Coupling Rates in Liquid-Phase Peptide Synthesis Using Competition Experiments", International Journal of Peptide Protein Research, 13: 274-277, 1979.
Neuberger "Generating High-Avidity Human Mabs in Mice", Nature Biotechnology, 14: 826, 1996.
Novials et al. "Reduction of Islet Amylin Expression and Basal Secretion by Adenovirus-Mediated Delivery of Amylin Antisense cDNA", Pancreas, 17(2): 182-186, 1998.
Offen et al. "A Low Molecular Weight Copper Chelator Crosses the Blood-Brain Barrier and Attenuates Experimental Autoimmune Encephalomyelitis", Journal of Neurochemistry, 89: 1241-1251, 2004.
Orlandi et al. "Cloning Immunoglobulin Variable Domains for Expression by the Polymerase Chain Reaction", Proc. Natl. Acad. Sci. USA, 86: 3833-3837, 1989.
Pack et al. "Improved Bivalent Miniantibodies, With Identical Avidity as Whole Anitbodies, Produced by High Cell Density Fermentation of *Escherichia coli*", Bio/Technology, 11: 1271-1277, 1993.
Pavia et al. "Antimicrobial Activity of Nicotine Against a Spectrum of Bacterial and Fungal Pathogens", Journal of Medical Microbiology, 49(7): 675-676, 2000.
Perbal "A Practical Guide to Molecular Cloning", Wiley-Interscience Publication.
Petkova et al. "A Structural Model for Alzheimer's β-Amyloid Fibrils Based on Experimental Constraints From Solid State NMR", Proc. Natl. Acad. Sci. USA, 99(26): 16742-16747, 2002.
Pettmann et al. "Morphological and Biochemical Maturation of Neurones Cultured in the Absence of Glial Cells", Nature, 281: 378-380, 1979.
Pinkert et al. "An Albumin Enhancer Located 10 Kb Upstream Functions Along With Its Promoter to Direct Efficient, Liver-Specific Expression in Transgenic Mice", Genes & Development, 1: 268-276, 1987.
Pispisa et al. "A Spectroscopic and Molecular Mechanics Investigation on a Series of AIB-Based Linear Peptides and a Peptide Template, Both Containing Tryptophan and a Nitroxide Derivative as Probes", Biopolymers, 53: 169-181, 2000.
Porter "The Hydrolysis of Rabbit γ-Globulin and Antibodies With Crystalline Papain", Biochemical Journal, 73: 119-126, 1959.
Presta "Antibody Engineering", Current Opinion in Structural Biology, 2: 593-596, 1992.
Puchtler et al. "A Review of Early Concepts of Amyloid in Context With Contemporary Chemical Literature From 1839 to 1859", The Journal of Histochemistry and Cytochemistry, 14(2): 123-134, 1966.
Reches et al. "Amyloid Fibril Formation by Pentapeptide and Tetrapeptide Fragments of Human Calcitonin", The Journal of Biological Chemistry, XP002276670, 277(38): 35475-35480, 2002.
Reza et al "Self-Assembling Organic Nanotubes Based on a Cyclic Peptide Architecture", Nature, 366: 324-327, 1993.
Riechmann et al. "Reshaping Human Antibodies for Therapy", Nature, 332: 323-329, 1988.
Sambrook et al. "Molecular Cloning: A Laboratory Manual", 2nd Edition, Cold Spring Harbor Laboratory,1989.
Sano "Prevention of Alzheimer's Disease: Where We Stand", Current Neurology and Neuroscience Reports, 2(5): 392-399, Oct. 2002. Abstract.
Seino "S20G Mutation of the Amylin Gene Is Associated With Type II Diabetes in Japanes", Diabetologia, 44: 906-909, 2001.
Shetty et al. "Aromatic π-Stacking in Solution as Revealed Through the Aggregation of Phenylacetylene Macrocycles", Journal of the American Chemical Society, 118: 1019-1027, 1996.
Sigel-Causey et al. "Phylogeny of the Pelecaniformes: Molecular Systematics of a Privative Group", Avian Molecular Evolution and Systematics, academic Press, p. 159-171, NBCI GenBank, Accession No. AAB58518, 1997.
Sigma "Alphabetical List of Compounds: Phe-Phe, Phe-Pro, Phe-Val", Biochemicals and Reagents for Life Science Research, p. 774, 2000-2001.
Solomon et al. "Disaggregation of Alzheimer β-Amyloid by Site-Directed MAb", Proc. Natl. Acad. Sci. USA, 94: 4109-4112, 1997.
Soto et al. "Beta-Sheet Breaker Peptides Inhibit Fibrillogenesis in a Rat Brain Model of Amyloidosis: Implications for Alzheimer's Therapy", Nature Medicine, 4(7): 822-826, 1998.
Soto et al. "Inhibition of Alzheimer's Amyloidosis by Peptides That Prevent β-Sheet Conformation", Biochemical and Biophysical Research Communications, 226(3): 672-680, 1996.
Stephenson et al. "The 'Promiscuous Drug Concept' With Applications to Alzheimer's Disease", FEBS Letters, 579: 1338-1342, 2005.
Stites et al. "Tables of Content", Basic & Clinical Immunology, 8th Ed.: 12 P.
Sun et al. "Aromatic Van der Waals Clusters: Structure and Nonrigidity", Journal of Physical Chemistry, 100: 13348-13366, 1996.
Tenidis et al. "Identification of a Penta- and Hexapeptide of Islet Amyloid Polypeptide (IAPP) With Amyloidogenic and Cytotoxic Propereties", Journal of Molecular Biology, 295(4): 1055-1071, 2000.
Tjernberg et al. "Arrest of β-Amyloid Fibril Formation by a Pentapeptide Ligand", The Journal of Biological Chemistry, 271(15): 8545-8548, 1996.
Tjernberg et al. "Controlling Amyloid β-Peptide Fibril Formation With Protease-Stable Ligands", The Journal of Biological Chemistry, 272(19): 12601-12605, 1997.

(56) References Cited

OTHER PUBLICATIONS

Toniolo et al. "Control of Peptide Conformation by the Thorpe-Ingold Effect (Cα-Tetrasubstitution)", Biopolymers (Peptide Science), 60(6): 396-419, 2001.
Tonkinson et al. "Antisense Oligodeoxynucleotides as Clinical Therapeutic Agents", Cancer Investigation, 14(1): 54-65, 1996.
Tsai et al. "Synthesis of AIB-Containing Peptidomimetics as Potential Inhibitors of Alzheimer's γ-Secretase", 218th ACS National Meeting, New Orleans, USA, Meeting Abstract, MEDI-018, 1999. Abstract.
Verhoeyen et al. "Reshaping Human Antibodies: Grafting an Antilysozyme Activity", Science, 239: 1534-1536, 1988.
Vidal et al. "A Stop-Codon Mutation in the BRI Gene Associated With Familial British Dementia", Nature, 399: 776-781, 1999.
Westermark "Amyloid and Polypeptide Hormones: What is Their Interrelationship?", Amyloid: International Journal of Experimental & Clinical Investigation, 1: 47-60, 1994.
Westermark "Islet Amyloid Polypeptide: Pinpointing Amino Acid Residues Linked to Amyloid Fibril Formation", Proc. Natl. Acad. Sci. USA, 87: 5036-5040, 1990.
Whitlow et al. "Single-Chain Fv Proteins and Their Fusion Proteins", Methods: A Companion to Methods in Enzymology, 2(2): 97-105, 1991.
Wilesmith et al. "Bovine Spongiform Encephalopathy", Current Topics in Microbiology & Immunology, 172: 21-38, 1991.
Winoto et al. "A Novel, Inducible and T Cell-Specific Enhancer Located at the 3' End of the T Cell Receptor Alpha Locus", The EMBO Journal, 8(3): 729-733, 1989.
Winter et al. "Man-Made Antibodies", Nature, 349: 293-299, 1991. No.
Wolfenden et al. "Affinities of Amino Acid Side Chains for Solvent Water", Biochemistry, 20: 849-855, 1981.
Yamada et al. "Study of the Enzymatic Degradation of Endomorphin Analogs Containing α, α-Disubstituted Glycine", Peptide Science, 2000: 421-424, 2001.
Examiner's Report Dated Feb. 11, 2010 From the Australian Government, IP Australia Re.: Application No. 2004251522.
Response Dated Feb. 7, 2010 to Notice of the Reason for Rejection of Oct. 22, 2009 From the Korean Intellectual Property Office Re.: Application No. 2004-7011868.
Response Dated Feb. 14, 2010 to Supplementary Partial European Search Report of Dec. 9, 2009 From the European Patent Office Re.: Application No. 04744917.8.
Response Dated Jan. 14, 2010 to Notice of the Reason for Rejection of Oct. 22, 2009 From the Korean Intellectual Property Office Re.: Application No. 2004-7011868.
Supplementary Partial European Search Report Dated Dec. 9, 2009 From the European Patent Office Re.: Application No. 04744917.8.
Translation of Notice of Reason for Rejection Dated Mar. 9, 2010 From the Japanese Patent Office Re.: Application No. 2006-518484.
Translation of Notice of the Reason for Rejection Dated Oct. 22, 2009 From the Korean Intellectual Property Office Re.: Application No. 2004-7011868.
Translation of Official Decision of Rejection Dated Dec. 4, 2009 From the Japanese Patent Office Re.: Application No. 2003-563456.
Vescovi et al. "Synthesis and Functional Studies of THF-Gramicidin Hybrid Ion Channels", Organic & Biomolecular Chemistry, 1(16): 2983-2997, Aug. 21, 2003.
International Search Report and the Written Opinion Dated Mar. 28, 2006 From the International Searching Authority Re.: Application No. PCT/IL2005/000754.
Office Action Dated Nov. 5, 2009 From the Israel Patent Office Re.: Application No. 172788 and Its Translation Into English.
Response Dated Apr. 6, 2010 to Office Action of Nov. 5, 2009 From the Israel Patent Office Re.: Application No. 172788.
Fingl et al. "Inroduction: General Principles", The Pharmacological Basis of Therapeutics, 5th Ed., Sec.I(Chap.1): 1-53, 1975.
Response Dated Sep. 14, 2010 to Official Action of Jun. 14, 2010 From the US Patent and Trademark Office Re.: U.S. Appl. No. 12/458,163.

Communication Pursuant to Article 94(3) EPC Dated Apr. 14, 2010 From the European Patent Office Re.: Application No. 03704977.2.
Response Dated Aug. 2, 2010 to Notice of Reason for Rejection of Mar. 9, 2010 From the Japanese Patent Office Re.: Application No. 2006-518484.
Response Dated Aug. 5, 2010 to Communication Pursuant to Article 94(3) EPC of Apr. 14, 2010 From the European Patent Office Re.: Application No. 03704977.2.
Examiner's Report Dated Apr. 7, 2011 From the Australian Government, IP Australia Re. Application No. 2004251522.
Restriction Official Action Dated Jul. 31, 2012 From the US Patent and Trademark Office Re. U.S. Appl. No. 11/632,410.
Mason et al. "Design Strategies for Anti-Amyloid Agents", Current Opinion in Structural Biology, 13: 1-7, 2003.
Office Action Dated Nov. 27, 2011 From the Israel Patent Office Re. Application No. 210418 and Its Translation Into English.
Translation of Office Action Dated Dec. 16, 2011 From the State Intellectual Property Office of the People's Republic of China Re. Application No. 2004800248446.3.
International Search Report and the Written Opinion Dated Jan. 31, 2012 From the International Searching Authority Re. Application No. PCT/IL2011/050010.
Translation of Final Notice of the Reason for Rejection Dated Jan. 19, 2012 From the Korean Intellectual Property Office Re. Application No. 2005-7025408.
Examiner's Report Dated Jan. 17, 2011 From the Australian Government, IP Australia Re.: Application No. 2004251522.
Notice of Allowance Dated Dec. 10, 2010 From the US Patent and Trademark Office Re.: U.S. Appl. No. 12/458,163.
Response Dated Jan. 2, 2011 to Office Action of Sep. 2, 2010 From the Israel Patent Office Re. Application No. 172788.
Response Dated Dec. 5, 2010 to Examiner's Report of Feb. 11, 2010 From the Australian Government, IP Australia Re.: Application No. 2004251522.
Response Dated Dec. 5, 2010 to Office Action of Aug. 24, 2010 From the State Intellectual Property Office of the People's Republic of China Re. Application No. 2004800248446.3.
Response Dated Jan. 20, 2011 to Requisition by the Examiner of Aug. 3, 2010 From the Canadian Intellectual Property Office Re. Application No. 2,473,987.
Response Dated Dec. 28, 2010 to Office Action of Sep. 2, 2010 From the Israeli Patent Office Re.: Application No. 163285.
Translation of Office Action Dated Aug. 24, 2010 From the State Intellectual Property Office of the People's Republic of China Re. Application No. 2004800248446.3.
McLaurin et al. "Cyclohexanehexol Inhibitors of A? Aggregation Prevent and Reverse Alzheimer Phenotype in a Mouse Model", Nature Medicine, 12(7): 801-808, Jul. 2006.
Yang et al. "Curcumin Inhibits Formation of Amyloid ? Oligomers and Fibrils, Binds Plaques, and Reduces Amyloid In Vivo", The Journal of Biological Chemistry, 280(7): 5892-5901, Feb. 18, 2005.
European Search Report and the European Search Opinion Dated Mar. 16, 2011 From the European Patent Office Re. Application No. 10191253.3.
Response Dated Mar. 2, 2011 to Examiner's Report of Jan. 17, 2011 From the Australian Government, IP Australia Re.: Application No. 2004251522.
Frydman-Marom et al. "Cognitive-Performance Recovery of Alzheimer's Disease Model Mice by Modulation of Early Soluble Amyloidal Assemblies", Angewnadte Chemie, International Edition, XP002601658, 48(11): 1981-1986, Jan. 1, 2009. p. 1985, col. 1, Line 4-p. 1986, col. 1, Line 4, Fig.1.
Trivedi et al. "Second Generation 'Peptoid' CCK-B Receptor Antagonists: Identification and Development of N-(Adamantyloxycarbonyl)-α-Methyl-(R)-Tryptophan Derivative (CI-1015) With an Improved Pharmacokinetic Profile", Journal of Medicinal Chemistry, XP002625505, 41: 38-45, Jan. 1, 1998.
Translation of Official Decision of Rejection Dated Apr. 3, 2012 From the Japanese Patent Office Re.: Application No. 2006-518484.
Balaram "De Novo Design: Backbone Conformational Constraints in Nucleating Helices and Beta-Hairpins", Journal of Peptide Research, 54: 195-199, 1999.

(56) References Cited

OTHER PUBLICATIONS

Restriction Official Action Dated Apr. 27, 2012 From the US Patent and Trademark Office Re. U.S. Appl. No. 12/654,461.
Office Action Dated Jun. 2, 2011 From the Israel Patent Office Re. Application No. 210418 and Its Translation Into English.
Translation of Notice of Reason for Rejection Dated Jun. 3, 2011 From the Japanese Patent Office Re.: Application No. 2006-518484.
Garofalo et al. "A Series of C-Terminal Amino Alcohol Dipeptide A? Inhibitors", Bioorganic & Medicinal Chemistry Letters, 12(21): 3051-3053, 2002.
Maji et al. "Fibril-Forming Model Synthetic Peptides Containing 3-Aminophenylacetic Acid", Tetrahedron, 58(43): 8695-8702, 2002.
Nadin et al. "Synthesis and γ-Secretase Activity of APP Substrate-Based Hydroxyethylene Dipeptide Isosteres", Bioorganic & Medicinal Chemistry Letters, 13(1): 37-41, Jan. 2003.
Reches et al. "Casting Metal Nanowires Within Discrete Self-Assembled Peptide Nanotubes", Science, 300: 625-627, Apr. 2003.
Requisition by the Examiner Dated Jun. 11, 2012 From the Canadian Intellectual Property Office Re. Application No. 2,473,987.
Translation of Decision on Rejection Dated Jun. 5, 2012 From the State Intellectual Property Office of the People's Republic of China Re. Application No. 200480024846.3.
Notice of Allowance Dated Mar. 10, 2011 From the Israel Patent Office Re. Application No. 163285.
Response Dated Jun. 9, 2011 to Notice of Allowance of Mar. 10, 2011 From the Israel Patent Office Re. Application No. 163285.
Response Dated Jun. 14, 2011 to Examination Report of Jan. 12, 2011 From the Government of India, Patent Office Re. Application No. 380/CHENP/2006.
Office Action Dated Jun. 20, 2012 From the Israel Patent Office Re. Application No. 172788 and Its Translation Into English.
Requisition by the Examiner Dated Jun. 30, 2011 From the Canadian Intellectual Property Office Re. Application No. 2,473,987.
Official Action Dated Sep. 27, 2012 From the US Patent and Trademark Office Re. U.S. Appl. No. 11/632,410.
Brown et al. "Human Spongiform Encephalopathy: The National Institutes of Health Series of 300 Cases of Experimentally Transmitted Disease", Annals of Neurology, 35(5): 513-529, May 1994.
Noursadeghi et al. "Role of Scrum Amyloid P. Component in Bacterial Infection: Protection of the Host or Protection of the Pathogen", Proc. Natl. Acad. Sci. USA, PNAS, 97(26): 14584-14589, Dec. 19, 2000.
Official Action Dated Oct. 3, 2012 From the US Patent and Trademark Office Re. U.S. Appl. No. 12/654,461.
Burger et al. "Incorporation of α-Trifluoromethyl Substituted [ALPHA]-Amino Acids Into C- and N-Terminal Position of Peptides and Peptide Mimetics Using Multicomponent Reactions", Tetrahedron, 54: 5915-5928, 1998.
Office Action Dated Nov. 3, 2011 From the Israel Patent Office Re. Application No. 172788 and its Translation Into English.
Response Dated Dec. 22, 2011 to Requisition by the Examiner of Jun. 30, 2011 From the Canadian Intellectual Property Office Re. Application No. 2,473,987.
Office Action Dated Sep. 2, 2010 From the Israel Patent Office Re. Application No. 172788 and Its Translation Into English.
Official Action Dated Oct. 5, 2010 From the US Patent and Trademark Office Re. U.S. Appl. No. 11/632,410.
Ausubel et al. Current Protocols in Molecular Biology, 1(Supp1.63).
Azriel et al. "Analysis of the Minimal Amyloid-Forming Fragment of the Islet Amyloid Polypeptide. An Experimental Support for the Key Role of the Phenylalanine Residue in Amyloid Formation", The Journal of Biological Chemistry, XP002555838, 276(36): 34156-34161, Sep. 7, 2001.
Balbach et al. "Supramolecular Structure in Full-Length Alzheimer's ?-Amyloid Fibrils: Evidence for A Parallel ?-Sheet Organization From Solid-State Nuclear Magnetic Resonance", Biophysical Journal, 83: 1205-1216, 2002.
Chopin et al. "Analysis of Six Prophages in *Lactococcus lactis* IL1403: Different Genetic Structure of Temperate and Virulent Phage Populations", Nucleic Acids Research, 29(3): 644-651, 2001.
Chou et al. "Conformational Parameters for Amino Acids in Helical, ?-Sheet, and Random Coil Regions Calculated From Proteins", Biochemistry, 13(2): 211-222, 1974.
Claessens et al. "Review Commentary: ?-? Interactions in Self-Assembly", Journal of Physical Organic Chemistry, 10: 254-272, 1997.
Findeis et al. "Modified-Peptide Inhibitors of Amyloid ?-Peptide Polymerization", Biochemistry, 38: 6791-6800, 1999.
Fishwild et al. "High-Avidity Hum IgG? Monoclonal Antibodies From a Novel Strain of Minilocus Transgenic Mice", Nature Biotechnology, 14: 845-851, 1996.
Grateau "Le Curli du Coli: Une Vari?t? Physiologique d'Amilose [Coli's Curli or How Amyloid Can be Physiological]", M?decine Sciences, 18(6-7): p. 664, 2002.
H?ggqvist et al. "Medin: An Integral Fragment of Aortic Smooth Muscle Cell-Produced Lactadherin Forms the Most Common Human Amyloid", Proc. Natl. Acad. Sci. USA, 96: 8669-8674, 1999.
H?ppener et al. "Islet Amyloid and Type 2 Diabetes Mellitus", The New England Journal of Medicine, 343(6): 411-419, 2000.
Hoeppener et al. "The Complete Islet Amyloid Polypeptide Precursor Is Encoded by Two Exons", Biochemical & Biophysical Research Communications, 189: 1569-1577, 1993. Database, Accession No. S04016, 1993. Claims 1-16, 22-26.
Hoogenboom et al. "By-Passing Immunisation. Human Antibodies From Synthetic Repertoires of Germline V? Gene Segments Rearranged In Vitro", Journal of Molecular Biology, 227: 381-388, 1992.
Jelokhani-Niaraki et al "Changes in Conformation and Antimicrobial Properties Caused by Replacement of D-Amino Acids With ?-Aminoisobutyric Acid in the Gramicidin Backbbone: Synthesis and Circular Dichroic Studies", Journal of the Chemical Society Perkin Transactions, 2: 1 187-1193, 1992.
Karle et al. "Structural Characteristics of ?-Helical Peptide Molecules Contianing Aib Residues", Biochemistry, 29(29): 6747-6756, Jul. 24, 1990.
Lowe et al. "Structure-Function Relationships for inhibitors of ?-Amyloid Toxicity Containing the Recognition Sequence KLVFF", Biochemistry, 40: 7882-7889, 2001.
McGaughey et al. "?-Stacking Interactions. Alive and Well in Proteins", The Journal of Biological Chemistry, 273(25): 15458-15463, Jun. 19, 1998.
Mosselman et al. "The Complete Islet Amyloid Polypeptide Precursor Is Encoded by Two Exons", FEBS Letters, 247: 154-158, 1989, Database Accession No. S04016.
Petkova et al. "A Structural Model for Alzheimer's ?-Amyloid Fibrils Based on Experimental Constraints From Solid State NMR", Proc. Natl. Acad. Sci. USA, 99(26): 16742-16747, 2002.
Porter "The Hydrolysis of Rabbit ?-Globulin and Antibodies With Crystalline Papain", Biochemical Journal, 73: 119-126, 1959.
Seino "S20G Mutation of the Amylin Gene Is Associated With Type II Diabetes in Japanes", Diahetologia, 44: 906-909, 2001.
Shetty et al. "Aromatic ?-Stacking in Solution as Revealed Through the Aggregation of Phenylacetylene Macrocycles", Journal of the American Chemical Society, 118: 1019-1027, 1996.
Solomon et al. "Disaggregation of Alzheimer ?-Amyloid by Site-Directed MAb", Proc. Natl. Acad. Sci. USA, 94: 4109-4112, 1997.
Soto et al. "Inhibition of Alzheimer's Amyloidosis by Peptides That Prevent ?-Sheet Conformation", Biochemical and Biophysical Research Communications, 226(3): 672-680, 1996.
Tjernberg et al. "Arrest of ?-Amyloid Fibril Formation by a Pentapeptide Ligand", The Journal of Biological Chemistry, 271(15): 8545-8548, 1996.
Tjernberg et al. "Controlling Amyloid ?-Peptide Fibril Formation With Protease-Stable Ligands", The Journal of Biological Chemistry, 272(19): 12601-12605, 1997.
Toniolo et al. "Control of Peptide Conformation by the Thorpe-Ingold Effect (C?-Tetrasubstitution)", Biopolymers (Peptide Science), 60(6): 396-419, 2001.
Tsai et al. "Synthesis of AIB-Containing Peptidomimetics as Potential Inhibitors of Alzheimer's ?-Secretase", 218th ACS National Meeting, New Orleans, USA, Meeting Abstract, MEDI-018, 1999. Abstract.
Yamada et al. "Study of the Enzymatic Degradation of Endomorphin Analogs Containing ?,?-Disubstituted Glycine", Peptide Science, 2000: 421-424, 2001.

(56) References Cited

OTHER PUBLICATIONS

Zaidi et al. "Forty Years of Calcitonin—Where Are We Now? A Tribute to the Work of Iain Macintyre, FRS", Bone, 30(5): 655-663, 2002.
Office Action Dated Mar. 4, 2013 From the Israel Patent Office Re. Application No. 222001 and Its Translation Into English.
Examination Report Dated Jan. 12, 2011 From the Government of India, Patent Office Re. Application No. 380/CHENP/2006.
Response Dated May 5, 2011 to Examiner's Report of Apr. 7, 2011 From the Australian Government, IP Australia Re. Application No. 2004251522.
Notice of Acceptance Dated Jun. 2, 2011 From the Australian Government, IP Australia Re. Application No. 2004251522.
Requisition by the Examiner Dated May 5, 2011 From the Canadian Intellectual Property Office Re. Application No. 2,530,927.
Requisition by the Examiner Dated Oct. 9, 2012 From the Canadian Intellectual Property Office Re. Application No. 2,530,927.
Official Action Dated Jan. 24, 2013 From the US Patent and Trademark Office Re. U.S. Appl. No. 11/632,410.
Official Action Dated Apr. 8, 2013 From the US Patent and Trademark Office Re. U.S. Appl. No. 11/632,410.
Office Action Dated Apr. 11, 2011 From the Israel Patent Office Re. Application No. 172788 and Its Translation Into English.
Office Action Dated Apr. 11, 2011 From the Israeli Patent Office Re.: Application No. 172788 and Its Translation Into English.
Translation of Notice of the Reason for Rejection Dated Apr. 25, 2011 From the Korean Intellectual Property Office Re. Application No. 2005-7025408.
Response Dated Jun. 29, 2011 to the Notice of the Reason for Rejection of Apr. 25, 2011 From the Korean Intellectual Property Office Re. Application No. 2005-7025408.
Official Action Dated Sep. 29, 2010 From the US Patent and Trademark Office Re.: U.S. Appl. No. 11/883,028.
Response Dated Oct. 2, 2011 to Office Action of Jun. 2, 2011 From the Israel Patent Office Re. Application No. 210418.
Office Action Dated Sep. 2, 2010 From the Israeli Patent Office Re.: Application No. 163285 and Its Translation Into English.
Response Dated Oct. 26, 2010 to Official Action of Oct. 5, 2010 From the US Patent and Trademark Office Re. U.S. Appl. No. 11/632,410.
Requisition by the Examiner Dated Jun. 25, 2013 From the Canadian Intellectual Property Office Re. Application No. 2,530,927.
Schoetz et al. "Determination of the Cis-Trans Isomerization Barrier of Several L-Peptidyl-L-Proline Dipeptides by Dynamic Capillary Electrophoresis and Computer Simulation", Electrophoresis, 22(12): 2409-2415, Aug. 1, 2001.

Rodent  KCNTATCATQRLANFLVRSSNNLGPVLPPTNVGSNTY  SEQ ID NO: 24
             1                                37
Human   KCNTATCATQRLANFLVHSSNNFGAILSSTNVGSNTY  SEQ ID NO: 25

| | | |
|---|---|---|
| wt | NH2-NFGAILSS-COOH | SEQ ID NO: 1 |
| N1A | NH2-AFGAILSS-COOH | SEQ ID NO: 2 |
| F2A | NH2-NAGAILSS-COOH | SEQ ID NO: 3 |
| G3A | NH2-NFAAILSS-COOH | SEQ ID NO: 4 |
| I5A | NH2-NFGAALSS-COOH | SEQ ID NO: 5 |
| L6A | NH2-NFGAIASS-COOH | SEQ ID NO: 6 |

A

B

C

METHOD OF SCREENING FOR COMPOUNDS THAT DISAGGREGATE AMYLOID AGGREGATES

RELATED APPLICATION

This Application is a divisional of pending U.S. patent application Ser. No. 11/656,542, filed on Jan. 23, 2007, which is a continuation of U.S. patent application Ser. No. 10/235,852, filed on Sep. 6, 2002, now abandoned, the contents of which are hereby incorporated by reference.

FIELD AND BACKGROUND OF THE INVENTION

The present invention relates to peptides, which can be used to diagnose, prevent, and treat amyloid-associated diseases, such as Type II diabetes mellitus.

Amyloid material deposition (also referred to as amyloid plaque formation) is a central feature of a variety of unrelated pathological conditions including Alzheimer's disease, prion-related encephalopathies, type II diabetes mellitus, familial amyloidosis and light-chain amyloidosis.

Amyloid material is composed of a dense network of rigid, nonbranching proteinaceous fibrils of indefinite length that are about 80 to 100 Å in diameter. Amyloid fibrils contain a core structure of polypeptide chains arranged in antiparallel β-pleated sheets lying with their long axes perpendicular to the long axis of the fibril [Both et al. (1997) Nature 385:787-93; Glenner (1980) N. Eng. J. Med. 302:1283-92].

Approximately twenty amyloid fibril proteins have been identified in-vivo and correlated with specific diseases. Amyloid proteins share little or no amino acid sequence homology, however the core structure of the amyloid fibrils is essentially the same.

The common core structure of amyloid fibrils and the presence of common substances in amyloid deposits suggest that data characterizing a particular form of amyloid material may also be relevant to other forms of amyloid material and thus can be implemented in template design for the development of drugs against amyloid-associated diseases such as type II diabetes mellitus, Alzheimer's dementia or diseases and prion-related encephalopathies.

Type II diabetes mellitus is a heterogeneous and multifactoral disease characterized by abnormalities in the action of insulin (i.e., insulin resistance) and the secretion of insulin (i.e., beta-cell failure). The relative contribution of each abnormality varies among patients as well as during the course of the disease [Ferrannini (1998) Endocr. Rev. 19:477-90].

Apparently, deposition of islet amyloid is involved in the pathogenesis of type II diabetes. Islet amyloidosis in patients with type II diabetes is associated with a reduced mass of insulin-producing beta cells and is most likely an important factor in the development of beta cell failure. Patients who require insulin treatment have the greatest reduction in islet mass and the most prominent amyloid deposits, indicating that the degree of islet amyloidosis may be related to the severity of the disease [Westermark (1994) Amyloid 1:47-60]. A link between islet amyloidosis and type II diabetes is further supported by the finding of islet amyloid in other animal species in which type II diabetes occurs, notably monkeys and cats [Westermark et al. (1990) Proc. Natl. Acad. Sci. USA 87:5036-40].

The building block of islet amyloid fibrils is a 37 amino acid residue peptide known as islet amyloid polypeptide [IAPP, Johnson et al. (1989) N. Eng. J. Med. 321:513-8]. The nucleotide sequence of the gene indicates that the islet amyloid polypeptide in normal subjects is identical to the islet amyloid polypeptide in amyloid deposits in diabetic patients. This finding suggests that a change in the amino acid sequence of islet amyloid polypeptide is not the pathogenic mechanism that leads to the formation of islet amyloid fibrils [Mosselman et al. (1988) FEBS Lett. 239:227-32].

However, comparison of the amino acid sequences of islet amyloid polypeptide among various animal species, in some of which islet amyloid does not develop, in combination with experiments involving in vitro formation of fibrils from synthetic islet amyloid polypeptide molecules has led to the identification of an "amyloidogenic" region within the human islet amyloid polypeptide molecule that is essential for the formation of fibrils [Johnson et al. (1989) N. Eng. J. Med. 321:513-8; Moriarty et al. (1999) Biochemistry 38:1811-8].

As suggested supra, islet amyloidosis is involved in the loss of up to 50% of beta cell mass in the pancreatic tissue of patients with type II diabetes as well as in diabetic cats and transgenic mice that produce human islet amyloid polypeptide [Hoppener et al. (2000) N. Eng. J. Med. 343:411-19].

Preventing or arresting the process of amyloid-related beta-cell failure at an early stage of type II diabetes might preserve endogenous insulin production and prevent or at least delay hyperglycemia.

Furthermore, it was found that mutations in the IAPP gene are correlated with predisposition and early onset of type II diabetes [Seino (2001) Diabetologia 44:906-9]. While Type II diabetes usually occurs at the age of 50 and higher, individuals with the genetic predisposition may be diagnosed with diabetes at their 30s. Therefore, prevention of amyloid formation may serve as a prophylactic treatment for such individuals (e.g., about 1% of the Far Asian population (China, Korea, Japan, and Taiwan).

Amyloid deposits do not appear to be inert in vivo, but rather are in a dynamic state of turnover and can even regress if the formation of fibrils is halted [Gillmore et al. (1997) Br. J. Haematol. 99:245-56].

Thus, therapies designed to inhibiting the production of human islet amyloid polypeptide or inhibiting amyloidosis may be useful for treating type II diabetes mellitus.

Inhibition of the Production of Islet Amyloid Polypeptide—

Both human islet amyloid gene and insulin share common promoter elements [Mosselman et al. (1988) FEBS Lett. 239:227-32]. Thus, the design of drugs, which inhibit the expression of the islet amyloid polypeptide gene without simultaneously inhibiting the expression of the insulin gene has not been attempted. Nevertheless, direct inhibition of the production of islet amyloid polypeptide may be accomplished through the use of antisense oligonucleotides against human islet amyloid polypeptide messenger RNA (mRNA). In vitro, the addition of antisense oligonucleotides or the expression of antisense complementary DNA against islet amyloid polypeptide mRNA increased the insulin mRNA and protein content of cells, demonstrating the potential effectiveness of this approach [Kulkarni et al. (1996) J. Endocrinol. 151:341-8; Novials et al. (1998) Pancreas 17:182-6]. However, no experimental results demonstrating the in vivo effectiveness of such antisense molecules have been demonstrated.

Inhibition of the Formation of Amyloid Fibrils—

Amyloid, including islet amyloid, contains potential stabilizing or protective substances, such as serum amyloid P component, apolipoprotein E, and perlecan. Blocking their binding to developing amyloid fibrils could inhibit amyloidogenesis [Kahn et al. (1999) Diabetes 48:241-53], as could treatment with antibodies specific for certain parts of an amyloidogenic protein [Solomon et al. (1997) Proc. Natl. Acad. Sci. USA 94:4109-12].

The following summarizes current attempts to engineer drugs having the capability of destabilizing amyloid structures.

Destabilizing Compounds—

Heparin sulfate has been identified as a component of all amyloids and has also been implicated in the earliest stages of inflammation-associated amyloid induction. Kisilevsky and co-workers (Mature Med. 1:143-148, 1995) described the use of low molecular weight anionic sulfonate or sulfate compounds that interfere with the interaction of heparin sulfate with the inflammation-associated amyloid precursor and the β peptide of Alzheimer's disease (AD). Heparin sulfate specifically influences the soluble amyloid precursor (SAA2) to adopt an increased β-sheet structure characteristic of the protein-folding pattern of amyloids. These anionic sulfonate or sulfate compounds were shown to inhibit heparin accelerated Aβ fibril formation and were able to disassemble preformed fibrils in vitro, as monitored by electron micrography. Moreover, these compounds substantially arrested murine splenic inflammation-associated amyloid progression in vivo in acute and chronic models. However, the most potent compound [i.e., poly-(vinylsulfonate)] showed acute toxicity. Similar toxicity has been observed with another compound, IDOX (Anthracycline 4'-iodo-4'-deoxy-doxorubicin), which has been observed to induce amyloid resorption in patients with immunoglobin light chain amyloidosis (AL) [Merlini et al. (1995) Proc. Natl. Acad. Sci. USA].

Destabilizing Antibodies—

Anti-β-amyloid monoclonal antibodies have been shown to be effective in disaggregating β-amyloid plaques and preventing β-amyloid plaque formation in vitro (U.S. Pat. No. 5,688,561). However, no experimental results demonstrating the in vivo effectiveness of such antibodies have been demonstrated.

Destabilizing Peptides—

The finding that the addition of synthetic peptides that disrupt the β-pleated sheets ("β-sheet breakers") dissociated fibrils and prevented amyloidosis [Soto et al. (1998) Nat. Med. 4:822-6] is particularly promising from a clinical point of view. In brief, a penta-residue peptide inhibited amyloid beta-protein fibrillogenesis, disassembled preformed fibrils in vitro and prevents neuronal death induced by fibrils in cell culture. In addition, the beta-sheet breaker peptide significantly reduced amyloid beta-protein deposition in vivo and completely blocked the formation of amyloid fibrils in a rat brain model of amyloidosis.

While reducing the present invention to practice, the present inventors have demonstrated that contrary to the teachings of U.S. Pat. No. 6,359,112 to Kapurniotu, peptide aggregation into amyloid fibrils is governed by aromatic interactions. Such findings enable to efficiently and accurately design peptides which can be used to diagnose and treat amyloid-associated diseases.

SUMMARY OF THE INVENTION

According to one aspect of the present invention there is provided a peptide comprising at least 5 amino acid residues and less than 15 amino acid residues, the peptide including an amino acid sequence as set forth in SEQ ID NO: 7.

According to another aspect of the present invention there is provided a peptide comprising at least 5 amino acid residues and less than 15 amino acid residues, the peptide including an amino acid sequence as set forth SEQ ID NO: 13, wherein the peptide is capable of forming self-aggregates under physiological conditions.

According to yet another aspect of the present invention there is provided a peptide selected from the group consisting of SEQ ID NOs: 8, 9, 10 and 11.

According to still another aspect of the present invention there is provided a peptide having an amino acid sequence set forth in SEQ ID NO: 13.

According to an additional aspect of the present invention there is provided a method of treating or preventing an amyloid-associated disease in an individual, the method comprising providing to the individual a therapeutically effective amount of a peptide having at least 5 amino acid residues and less than 15 amino acid residues, the peptide including an amino acid sequence as set forth in SEQ ID NO: 7.

According to yet additional aspect of the present invention there is provided a method of treating or preventing an amyloid-associated disease in an individual, the method comprising providing to the individual therapeutically effective amount of a peptide having at least 5 amino acid residues and less than 15 amino acid residues, the peptide including an amino acid sequence as set forth in SEQ ID NO: 13 and being capable of self aggregating under physiological conditions.

According to still additional aspect of the present invention there is provided a method of treating or preventing an amyloid-associated disease in an individual, the method comprising providing to the individual a therapeutically effective amount of a peptide selected from the group consisting of SEQ ID NOs: 8, 9, 10 and 11, wherein the peptide is an active ingredient of a pharmaceutical compositions which also includes a physiologically acceptable carrier.

According to a further aspect of the present invention there is provided a method of treating or preventing an amyloid-associated disease in an individual, the method comprising providing to the individual a therapeutically effective amount of a peptide having the amino acid sequence set forth in SEQ ID NO: 13 wherein the peptide is an active ingredient of a pharmaceutical compositions which also includes a physiologically acceptable carrier.

According to yet a further aspect of the present invention there is provided a pharmaceutical composition for treating or preventing an amyloid-associated disease comprising as an active ingredient a peptide having at least 5 amino acid residues and less than 15 amino acid residues, the peptide including an amino acid sequence as set forth in SEQ ID NO: 7 and a pharmaceutically acceptable carrier or diluent.

According to still a further aspect of the present invention there is provided a pharmaceutical composition for treating or preventing an amyloid-associated disease comprising as an active ingredient a peptide selected from the group consisting of SEQ ID NOs: 8, 9, 10 and 111 and a pharmaceutically acceptable carrier or diluent.

According to still a further aspect of the present invention there is provided a pharmaceutical composition for treating or preventing an amyloid-associated disease comprising as an active ingredient a peptide having the amino acid sequence set forth in SEQ ID NO: 13 and a pharmaceutically acceptable carrier or diluent.

According to still a further aspect of the present invention there is provided a nucleic acid construct comprising a polynucleotide segment encoding a peptide selected from the group consisting of SEQ ID NOs: 8, 9, 10 and 11.

According to still a further aspect of the present invention there is provided a nucleic acid construct comprising a polynucleotide segment encoding a peptide having the amino acid sequence set forth in SEQ ID NO: 13.

According to still a further aspect of the present invention there is provided a nucleic acid construct comprising a polynucleotide segment encoding a peptide having at least 5 amino acid residues and less than 15 amino acid residues, the peptide including an amino acid sequence as set forth in SEQ ID NO: 7.

According to further features in preferred embodiments of the invention described below, the amino acid sequence is selected from the group consisting of SEQ ID NO: 4, 12 and 13.

According to still further features in the described preferred embodiments the peptide is as set forth in SEQ ID NO: 13.

According to still further features in the described preferred embodiments the peptide is as set forth in SEQ ID NO: 12.

According to still further features in the described preferred embodiments the peptide further comprising at least two serine residues at a C-terminus thereof.

According to still further features in the described preferred embodiments the peptide is a linear or cyclic peptide.

According to still further features in the described preferred embodiments the peptide is an active ingredient of a pharmaceutical composition which also includes a physiologically acceptable carrier.

According to still further features in the described preferred embodiments the peptide is expressed from a nucleic acid construct.

According to still further features in the described preferred embodiments the nucleic acid construct further comprising a promoter.

The present invention successfully addresses the shortcomings of the presently known configurations by providing novel peptides, compositions and methods, which can be used to diagnose and treat amyloid associated diseases such as type II Diabetes mellitus.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 1a is a sequence alignment of human and rodent IAPP. A block indicates a seven amino acid sub-sequence illustrating the major inconsistencies between the sequences. The "basic amyloidogenic unit" is presented by bold letters and underlined. FIG. 1b illustrates the chemical structure of the wild type IAPP peptide (SEQ ID NO: 1). FIG. 1c illustrates the primary sequences and SEQ ID NOs of the peptides of the present invention.

DESCRIPTION OF THE PREFERRED EMBODIMENTS

Figures 1A, 1B, 1C:
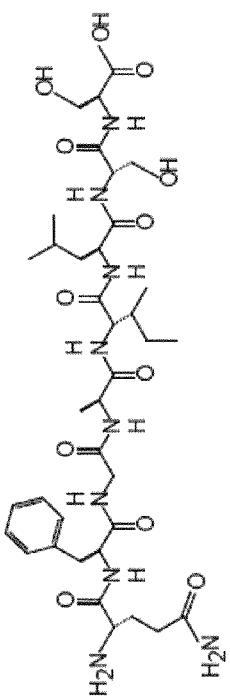
FIGS. 1a-c are schematic illustrations of a primary sequence comparison between human and rodent IAPP and the synthetic peptides of the present invention.

The present invention is of novel peptides, compositions and methods, which can be used to diagnose and treat amyloid associated diseases such as type II Diabetes mellitus.

The principles and operation of the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Numerous therapeutic approaches for prevention of amyloid fibril formation or disaggregation of amyloid material have been described in the prior art. However, current therapeutic approaches are limited by cytotoxicity, non-specificity and delivery barriers.

While reducing the present invention to practice and while searching for a novel therapeutic modality to amyloid associated diseases, in particular type II diabetes mellitus, the present inventors have identified a sequence characteristic of amyloid forming peptides which governs fibril formation.

Previous efforts to define the contributions of specific residues in the IAPP basic amyloidogenic sequence involved the use of site-directed deletion mutagenesis [U.S. Pat. No. 6,359,112 and Konstantinos et al. (2000) J. Mol. Biol. 295: 1055-71]. This approach resulted in the findings that the structural determinants for IAPP peptide assembly are consecutive glycine and alanine residues.

In sharp contrast, the present inventors have uncovered that the largest contribution to peptide aggregation comes from the aromatic residue of the peptide rather than from the glycine and alanine residues.

This discrepancy in results can be explained by the different biochemical approaches, which were utilized to elucidate the minimal amyloidogenic sequence. While Kapurniotu et al. implemented a deletion mutant analysis, which overlooks the need to retain tertiary structures [Konstantinos et al. (2000) J. Mol. Biol. 295:1055-71], the inventors of the present invention used an alanine scanning approach, wherein each alanine substitution examines the contribution of an individual amino acid side chain to the functionality of the protein, without extensively changing its hydrophobicity or tendency to form β-sheet structures (see Example 1 of the Examples section).

The present findings enable for the first time, to generate highly efficient diagnostic and therapeutic peptides which can be utilized to treat or diagnose diseases characterized by amyloid plaque formation.

Thus, according to one aspect of the present invention there is provided a peptide which preferably includes an amino acid sequence as set forth in SEQ ID NO: 7.

The sequence set forth in SEQ. ID NO: 7 includes at least one aromatic amino acid residue which, as is shown by the results presented in the Examples section, is pivotal to the formation of amyloid fibrils.

The aromatic amino acid can be any naturally occurring or synthetic aromatic residue including, but not limited to, phenylalanine, tyrosine, tryptophan, phenylglycine, or modificants, precursors or functional aromatic portions thereof. Examples of aromatic residues which can be used by the present invention are provided in Table 2 below.

As is demonstrated by the results provided in the Examples section which follows, the present invention facilitates the design of peptides exhibiting varying degrees of self-aggregation kinetics and aggregate structure.

As used herein, the phrase "self-aggregation" refers to the capability of a peptide to form aggregates (e.g. fibrils) in an aqueous solution. The ability of a peptide to self-aggregate and the kinetics and type of such self-aggregation determines a use for the peptide in treating or diagnosing amyloid diseases.

Since aggregation kinetics and aggregate structures are largely determined by the specific residue composition and possibly the length of the peptides generated, the present invention encompasses both longer peptides (e.g., 10-50 amino acids) which include the sequences set forth in SEQ ID NOs: 4, 12 or 13, or shorter peptides (5-10 amino acid residues) including any of these sequences. Due to their self-aggregating nature these peptides can be used as potent diagnostic reagents.

Alternatively, the peptides of the present invention include sequences set forth in SEQ ID NOs: 8, 9, 10 and 11.

For example, a peptide encompassed by SEQ ID NO: 9, 10 or 11 can be utilized for therapy since as is shown in the Examples section which follows, such a peptide displays no aggregation (SEQ ID NO: 9) or slow aggregation kinetics as compared to the wild type peptide (SEQ ID NOs: 9 and 10). It is conceivable that since amyloid formation is in any case a very slow process the peptides of the present invention will completely inhibit or significantly delay amyloidosis under physiological conditions.

The term "peptide" as used herein encompasses native peptides (either degradation products, synthetically synthesized peptides or recombinant peptides) and peptidomimetics (typically, synthetically synthesized peptides), as well as peptoids and semipeptoids which are peptide analogs, which may have, for example, modifications rendering the peptides more stable while in a body or more capable of penetrating into cells. Such modifications include, but are not limited to N terminus modification, C terminus modification, peptide bond modification, including, but not limited to, CH2-NH, CH2-S, CH2-S=O, O=C—NH, CH2-O, CH2-CH2, S=C—NH, CH=CH or CF=CH, backbone modifications, and residue modification. Methods for preparing peptidomimetic compounds are well known in the art and are specified, for example, in Quantitative Drug Design, C. A. Ramsden Gd., Chapter 17.2, F. Choplin Pergamon Press (1992), which is incorporated by reference as if fully set forth herein. Further details in this respect are provided hereinunder.

Peptide bonds (—CO—NH—) within the peptide may be substituted, for example, by N-methylated bonds (—N(CH3)-CO—), ester bonds (—C(R)H—C—O—O—C(R)—N—), ketomethylen bonds (—CO—CH2-), α-aza bonds (—NH—N(R)—CO—), wherein R is any alkyl, e.g., methyl, carba bonds (—CH2-NH—), hydroxyethylene bonds (—CH(OH)—CH2-), thioamide bonds (—CS—NH—), olefinic double bonds (—CH=CH—), retro amide bonds (—NH—CO—), peptide derivatives (—N(R)—CH2-CO—), wherein R is the "normal" side chain, naturally presented on the carbon atom.

These modifications can occur at any of the bonds along the peptide chain and even at several (2-3) at the same time.

Natural aromatic amino acids, Trp, Tyr and Phe, may be substituted for synthetic non-natural acid such as Phenylglycine, TIC, naphthylalanine (Nol), ring-methylated derivatives of Phe, halogenated derivatives of Phe or o-methyl-Tyr.

In addition to the above, the peptides of the present invention may also include one or more modified amino acids or one or more non-amino acid monomers (e.g. fatty acids, complex carbohydrates etc).

As used herein in the specification and in the claims section below the term "amino acid" or "amino acids" is understood to include the 20 naturally occurring amino acids; those amino acids often modified post-translationally in vivo, including, for example, hydroxyproline, phosphoserine and phosphothreonine; and other unusual amino acids including, but not limited to, 2-aminoadipic acid, hydroxylysine, isodemosine, nor-valine, nor-leucine and ornithine. Furthermore, the term "amino acid" includes both D- and L-amino acids.

Tables 1 and 2 below list naturally occurring amino acids (Table 1) and non-conventional or modified amino acids (Table 2) which can be used with the present invention.

TABLE 1

| Amino Acid | Three-Letter Abbreviation | One-letter Symbol |
|---|---|---|
| alanine | Ala | A |
| Arginine | Arg | R |
| Asparagine | Asn | N |
| Aspartic acid | Asp | D |
| Cysteine | Cys | C |
| Glutamine | Gln | Q |
| Glutamic Acid | Glu | E |
| glycine | Gly | G |
| Histidine | His | H |
| isoleucine | Iie | I |
| leucine | Leu | L |
| Lysine | Lys | K |
| Methionine | Met | M |
| phenylalanine | Phe | F |
| Proline | Pro | P |
| Serine | Ser | S |
| Threonine | Thr | T |
| tryptophan | Trp | W |
| tyrosine | Tyr | Y |
| Valine | Val | V |
| Any amino acid as above | Xaa | X |

TABLE 2

| Non-conventional amino acid | Code | Non-conventional amino acid | Code |
|---|---|---|---|
| α-aminobutyric acid | Abu | L-N-methylalanine | Nmala |
| α-amino-α-methylbutyrate | Mgabu | L-N-methylarginine | Nmarg |
| aminocyclopropane-carboxylate | Cpro | L-N-methylasparagine | Nmasn |
|  |  | L-N-methylaspartic acid | Nmasp |
| aminoisobutyric acid | Aib | L-N-methylcysteine | Nmcys |
| aminonorbornyl-carboxylate | Norb | L-N-methylglutamine | Nmgln |
|  |  | L-N-methylglutamic acid | Nmglu |
| cyclohexylalanine | Chexa | L-N-methylhistidine | Nmhis |
| cyclopentylalanine | Cpen | L-N-methylisolleucine | Nmile |
| D-alanine | Dal | L-N-methylleucine | Nmleu |
| D-arginine | Darg | L-N-methyllysine | Nmlys |
| D-aspartic acid | Dasp | L-N-methylmethionine | Nmmet |
| D-cysteine | Dcys | L-N-methylnorleucine | Nmnle |
| D-glutamine | Dgln | L-N-methylnorvaline | Nmnva |
| D-glutamic acid | Dglu | L-N-methylornithine | Nmorn |
| D-histidine | Dhis | L-N-methylphenylalanine | Nmphe |
| D-isoleucine | Dile | L-N-methylproline | Nmpro |
| D-leucine | Dleu | L-N-methylserine | Nmser |
| D-lysine | Dlys | L-N-methylthreonine | Nmthr |
| D-methionine | Dmet | L-N-methyltryptophan | Nmtrp |
| D-ornithine | Dorn | L-N-methyltyrosine | Nmtyr |
| D-phenylalanine | Dphe | L-N-methylvaline | Nmval |
| D-proline | Dpro | L-N-methylethylglycine | Nmetg |
| D-serine | Dser | L-N-methyl-t-butylglycine | Nmtbug |
| D-threonine | Dthr | L-norleucine | Nle |
| D-tryptophan | Dtrp | L-norvaline | Nva |
| D-tyrosine | Dtyr | α-methyl-aminoisobutyrate | Maib |
| D-valine | Dval | α-methyl-γ-aminobutyrate | Mgabu |
| D-α-methylalanine | Dmala | α-methylcyclohexylalanine | Mchexa |
| D-α-methylarginine | Dmarg | α-methylcyclopentylalanine | Mcpen |
| D-α-methylasparagine | Dmasn | α-methyl-α-napthylalanine | Manap |
| D-α-methylaspartate | Dmasp | α-methylpenicillamine | Mpen |
| D-α-methylcysteine | Dmcys | N-(4-aminobutyl)glycine | Nglu |
| D-α-methylglutamine | Dmgln | N-(2-aminoethyl)glycine | Naeg |
| D-α-methylhistidine | Dmhis | N-(3-aminopropyl)glycine | Norn |
| D-α-methylisoleucine | Dmile | N-amino-α-methylbutyrate | Nmaabu |
| D-α-methylleucine | Dmleu | α-napthylalanine | Anap |
| D-α-methyllysine | Dmlys | N-benzylglycine | Nphe |
| D-α-methylmethionine | Dmmet | N-(2-carbamylethyl)glycine | Ngln |
| D-α-methylornithine | Dmorn | N-(carbamylmethyl)glycine | Nasn |
| D-α-methylphenylalanine | Dmphe | N-(2-carboxyethyl)glycine | Nglu |
| D-α-methylproline | Dmpro | N-(carboxymethyl)glycine | Nasp |
| D-α-methylserine | Dmser | N-cyclobutylglycine | Ncbut |
| D-α-methylthreonine | Dmthr | N-cycloheptylglycine | Nchep |
| D-α-methyltryptophan | Dmtrp | N-cyclohexylglycine | Nchex |
| D-α-methyltyrosine | Dmty | N-cyclodecylglycine | Ncdec |
| D-α-methylvaline | Dmval | N-cyclododeclglycine | Ncdod |
| D-α-methylalnine | Dnmala | N-cyclooctylglycine | Ncoct |
| D-α-methylarginine | Dnmarg | N-cyclopropylglycine | Ncpro |
| D-α-methylasparagine | Dnmasn | N-cycloundecylglycine | Ncund |
| D-α-methylasparatate | Dnmasp | N-(2,2-diphenylethyl)glycine | Nbhm |
| D-α-methylcysteine | Dnmcys | N-(3,3-diphenylpropyl)glycine | Nbhe |
| D-N-methylleucine | Dnmleu | N-(3-indolylyethyl) glycine | Nhtrp |
| D-N-methyllysine | Dnmlys | N-methyl-γ-aminobutyrate | Nmgabu |
| N-methylcyclohexylalanine | Nmchexa | D-N-methylmethionine | Dnmmet |
| D-N-methylornithine | Dnmorn | N-methylcyclopentylalanine | Nmcpen |
| N-methylglycine | Nala | D-N-methylphenylalanine | Dnmphe |
| N-methylaminoisobutyrate | Nmaib | D-N-methylproline | Dnmpro |
| N-(1-methylpropyl)glycine | Nile | D-N-methylserine | Dnmser |
| N-(2-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nva |
| D-N-methyltyrosine | Dnmtyr | N-methyla-napthylalanine | Nmanap |
| D-N-methylvaline | Dnmval | N-methylpenicillamine | Nmpen |
| γ-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | penicillamine | Pen |
| L-homophenylalanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α-methylglutamine | Mgln | L-α-methylglutamate | Mglu |
| L-α-methylhistidine | Mhis | L-α-methylhomo phenylalanine | Mhphe |
| L-α-methylisoleucine | Mile | N-(2-methylthioethyl)glycine | Nmet |
| D-N-methylglutamine | Dnmgln | N-(3-guanidinopropyl)glycine | Narg |
| D-N-methylglutamate | Dnmglu | N-(1-hydroxyethyl)glycine | Nthr |
| D-N-methylhistidine | Dnmhis | N-(hydroxyethyl)glycine | Nser |
| D-N-methylisoleucine | Dnmile | N-(imidazolylethyl)glycine | Nhis |

TABLE 2-continued

| Non-conventional amino acid | Code | Non-conventional amino acid | Code |
|---|---|---|---|
| D-N-methylleucine | Dnmleu | N-(3-indolylyethyl)glycine | Nhtrp |
| D-N-methyllysine | Dnmlys | N-methyl-γ-aminobutyrate | Nmgabu |
| N-methylcyclohexylalanine | Nmchexa | D-N-methylmethionine | Dnmmet |
| D-N-methylornithine | Dnmorn | N-methylcyclopentylalanine | Nmcpen |
| N-methylglycine | Nala | D-N-methylphenylalanine | Dnmphe |
| N-methylaminoisobutyrate | Nmaib | D-N-methylproline | Dnmpro |
| N-(1-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nval |
| D-N-methyltyrosine | Dnmtyr | N-methyla-napthylalanine | Nmanap |
| D-N-methylvaline | Dnmval | N-methylpenicillamine | Nmpen |
| γ-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | penicillamine | Pen |
| L-homophenylalanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α-methylglutamine | Mgln | L-α-methylglutamate | Mglu |
| L-α-methylhistidine | Mhis | L-α-methylhomophenylalanine | Mhphe |
| L-α-methylisoleucine | Mile | N-(2-methylthioethyl)glycine | Nmet |
| L-α-methylleucine | Mleu | L-α-methyllysine | Mlys |
| L-α-methylmethionine | Mmet | L-α-methylnorleucine | Mnle |
| L-α-methylnorvaline | Mnva | L-α-methylornithine | Morn |
| L-α-methylphenylalanine | Mphe | L-α-methylproline | Mpro |
| L-α-methylserine | mser | L-α-methylthreonine | Mthr |
| L-α-methylvaline | Mtrp | L-α-methyltyrosine | Mtyr |
| L-α-methylleucine | Mval Nnbhm | L-N-methylhomophenylalanine | Nmhphe |
| N-(N-(2,2-diphenylethyl) carbamylmethyl-glycine | Nnbhm | N-(N-(3,3-diphenylpropyl) carbamylmethyl(1)glycine | Nnbhe |
| 1-carboxy-1-(2,2-diphenyl ethylamino)cyclopropane | Nmbc | | |

Since the present peptides are preferably utilized in therapeutics or diagnostics which require the peptides to be in soluble form, the peptides of the present invention preferably include one or more non-natural or natural polar amino acids, including but not limited to serine and threonine which are capable of increasing peptide solubility due to their hydroxyl-containing side chain.

The peptides of the present invention are preferably utilized in a linear form, although it will be appreciated that in cases where cyclicization does not severely interfere with peptide characteristics, cyclic forms of the peptide can also be utilized.

Cyclic peptides can either be synthesized in a cyclic form or configured so as to assume a cyclic form under desired conditions (e.g., physiological conditions).

Thus, the present invention provides conclusive data as to the identity of the structural determinant of amyloid peptides, which directs fibril assembly.

As such, the present invention enables design of a range of peptide sequences, which can be utilized for prevention/treatment or diagnosis of amyloidosis.

Figure 6:
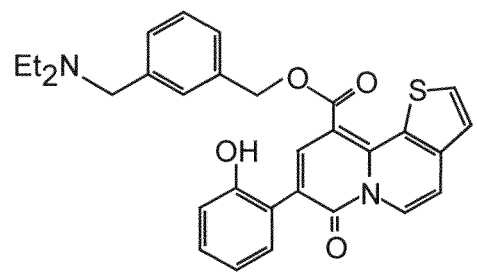
FIGS. 6a-c are schematic illustrations of amyloid binding with the inhibitory aromatic reagents: Ro 47-1816/001 (FIG. 6a), Thioflavin T (FIG. 6b) and CR dye (FIG. 6c).
Figure 6:
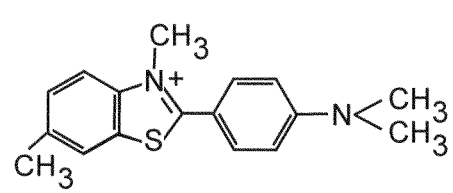
Figure 6:
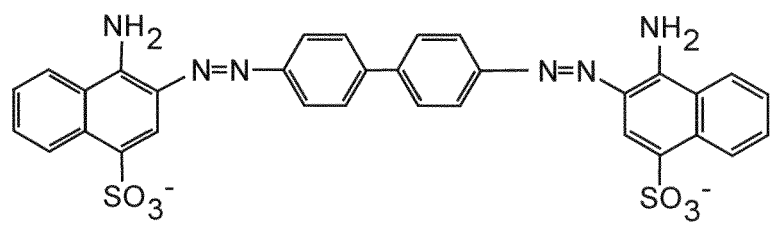

The results presented herein are further substantiated by the observation that the consensus aromatic sequence of the present invention (SEQ ID NO: 7) is shared by numerous amyloid related proteins (see Table 3), and the fact that small aromatic molecules, such as Ro 47-1816/001 [Kuner et al. (2000) J. Biol. Chem. 275:1673-8, see FIG. 6a] and 3-p-toluoyl-2-[4'-(3-diethylaminopropoxy)phenyl]-benzofuran [Twyman (1999) Tetrahedron Letters 40:9383-9384] have been demonstrated effective in inhibiting the polymerization of the beta polypeptide of Alzheimer's disease [Findeis et al. (2000) Biochem. Biophys. Acta 1503:76-84], while amyloid specific dyes such as Congo-Red (FIG. 6b) and thioflavin T (FIG. 6c), which contain aromatic elements are generic amyloid formation inhibitors.

As is mentioned hereinabove, one specific use for the peptides of the present invention is prevention or treatment of diseases associated with amyloid plaque formation.

Thus, according to another aspect of the present invention, there is provided a method of treating an amyloid-associated disease in an individual. Preferred individual subjects according to the present invention are mammals such as canines, felines, ovines, porcines, equines, bovines, humans and the like.

The term "treating" refers to reducing or preventing amyloid plaque formation, or substantially decreasing plaque occurrence in the affected tissue.

Amyloid-associated diseases treated according to the present invention include, but are not limited to, type II diabetes mellitus, Alzheimer's disease (AD), early onset Alzheimer's disease, late onset Alzheimer's disease, presymptomatic Alzheimer's disease, SAA amyloidosis, hereditary Icelandic syndrome, multiple myeloma, and prion diseases including scrapie of sheep and goats and bovine spongiform encephalopathy (BSE) of cattle [Wilesmith and Wells (1991) Curr Top Microbiol Immunol 172: 21-38] and human prion diseases including (i) kuru, (ii) Creutzfeldt-Jakob Disease (CJD), (iii) Gerstmann-Streussler-Sheinker Disease (GSS), and (iv) fatal familial insomnia (FFI) [Gajdusek (1977) Science 197: 943-960; Medori, Tritschler et al. (1992) N Engl J Med 326: 444-449].

The method includes providing to the individual a therapeutically effective amount of the peptide of the present invention.

It will be appreciated that when utilized for treatment of amyloid diseases, the peptide of the present invention includes an amino acid sequence suitable for preventing fibril formation, reducing fibril formation, or disaggregating formed aggregates by competitive destabilization of the pre-formed aggregate. For example, SEQ ID NO: 9 can be utilized for treatment of amyloid diseases, particularly type II diabetes mellitus since as shown in the Examples section which follows, such a sequence exhibits no amyloid fibril formation in an aqueous solution.

Alternatively, SEQ ID NOs: 10 or 11 can be used as potent inhibitors of type II diabetes since as shown in the Examples section which follows, substitution of either leucine or isoleucine in the peptide elicits very slow kinetics of aggregation. Since amyloid formation in vivo is a very slow process, it is conceivable that under physiological conditions no fibrilization will occur upon the substitution of isoleucine or leucine to alanine in the context of the full length IAPP.

The peptide (i.e., active ingredient) of the present invention can be provided to an individual per se, or as part of a pharmaceutical composition where it is mixed with a pharmaceutically acceptable carrier.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the preparation accountable for the biological effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases. One of the ingredients included in the pharmaceutically acceptable carrier can be for example polyethylene glycol (PEG), a biocompatible polymer with a wide range of solubility in both organic and aqueous media (Mutter et al. (1979).

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Suitable routes of administration may, for example, include oral, rectal, transmucosal, especially transnasal, intestinal or parenteral delivery, including intramuscular, subcutaneous and intramedullary injections as well as intrathecal, direct intraventricular, intravenous, intraperitoneal, intranasal, or intraocular injections.

Alternately, one may administer a preparation in a local rather than systemic manner, for example, via injection of the preparation directly into a specific region of a patient's body.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the invention may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethyl-cellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions, which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The preparations described herein may be formulated for parenteral administration, e.g., by bolus injection or continuos infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The preparation of the present invention may also be formulated in rectal compositions such as suppositories or retention enemas, using, e.g., conventional suppository bases such as cocoa butter or other glycerides.

Pharmaceutical compositions suitable for use in context of the present invention include compositions wherein the active ingredients are contained in an amount effective to achieve the intended purpose. More specifically, a therapeutically effective amount means an amount of active ingredients effective to prevent, alleviate or ameliorate symptoms of disease or prolong the survival of the subject being treated.

Determination of a therapeutically effective amount is well within the capability of those skilled in the art.

For any preparation used in the methods of the invention, the therapeutically effective amount or dose can be estimated initially from in vitro assays. For example, a dose can be formulated in animal models and such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. [See e.g., Fingl, et al., (1975) "The Pharmacological Basis of Therapeutics", Ch. 1 p. 1].

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

Compositions including the preparation of the present invention formulated in a compatible pharmaceutical carrier may also be prepared, placed in an appropriate container, and labeled for treatment of an indicated condition.

Compositions of the present invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert.

It will be appreciated that the peptides of the present invention can also be expressed from a nucleic acid construct administered to the individual employing any suitable mode of administration, described hereinabove (i.e., in-vivo gene therapy). Alternatively, the nucleic acid construct is introduced into a suitable cell via an appropriate gene delivery vehicle/method (transfection, transduction, homologous recombination, etc.) and an expression system as needed and then the modified cells are expanded in culture and returned to the individual (i.e., ex-vivo gene therapy).

To enable cellular expression of the peptides of the present invention, the nucleic acid construct of the present invention further includes at least one cis acting regulatory element. As used herein, the phrase "cis acting regulatory element" refers to a polynucleotide sequence, preferably a promoter, which binds a trans acting regulator and regulates the transcription of a coding sequence located downstream thereto.

Any available promoter can be used by the present methodology. In a preferred embodiment of the present invention, the promoter utilized by the nucleic acid construct of the present invention is active in the specific cell population transformed. Examples of cell type-specific and/or tissue-specific promoters include promoters such as albumin that is liver specific [Pinkert et al., (1987) Genes Dev. 1:268-277], lymphoid specific promoters [Calame et al., (1988) Adv. Immunol. 43:235-275]; in particular promoters of T-cell receptors [Winoto et al., (1989) EMBO J. 8:729-733] and immunoglobulins; [Banerji et al. (1983) Cell 33729-740], neuron-specific promoters such as the neurofilament promoter [Byrne et al. (1989) Proc. Natl. Acad. Sci. USA 86:5473-5477], pancreas-specific promoters [Edlunch et al. (1985) Science 230:912-916] or mammary gland-specific promoters such as the milk whey promoter (U.S. Pat. No. 4,873,316 and European Application Publication No. 264, 166). The nucleic acid construct of the present invention can further include an enhancer, which can be adjacent or distant to the promoter sequence and can function in up regulating the transcription therefrom.

The constructs of the present methodology preferably further include an appropriate selectable marker and/or an origin of replication. Preferably, the construct utilized is a shuttle vector, which can propagate both in $E.\ coli$ (wherein the construct comprises an appropriate selectable marker and origin of replication) and be compatible for propagation in cells, or integration in a gene and a tissue of choice. The construct according to the present invention can be, for example, a plasmid, a bacmid, a phagemid, a cosmid, a phage, a virus or an artificial chromosome.

Examples of suitable constructs include, but are not limited to pcDNA3, pcDNA3.1 (+/−), pGL3, PzeoSV2 (+/−), pDisplay, pEF/myc/cyto, pCMV/myc/cyto each of which is commercially available from Invitrogen Co. (www.invitrogen.com). Examples of retroviral vector and packaging systems are those sold by Clontech, San Diego, Calif., including Retro-X vectors pLNCX and pLXSN, which permit cloning into multiple cloning sites and the transgene is transcribed from CMV promoter. Vectors derived from Mo-MuLV are also included such as pBabe, where the transgene will be transcribed from the 5'LTR promoter.

Because of the self-aggregating nature of the peptides of the present invention it is conceivable that such peptides can also be used as potent detectors of amyloid fibrils/plaques in biological samples. This is of a special significance to amyloid-associated diseases such as Alzheimer's disease wherein unequivocal diagnosis can only be made after postmortem examination of brain tissues for the hallmark neurofibrillary tangles (NFT) and neuritic plaques.

Thus, according to yet another aspect of the present invention there is provided a method of detecting a presence or an absence of an amyloid fibril in a biological sample.

The method is effected by incubating the biological sample with a peptide of the present invention capable of co-aggregating with the amyloid fibril and detecting the peptide, to thereby detect the presence or the absence of amyloid fibril in the biological sample. A variety of peptide reagents, which are capable of recognizing conformational ensembles are known in the art some of which are reviewed in Bursavich (2002) J. Med. Chem. 45(3): 541-58 and in Baltzer Chem. Rev. 101(10):3153-63.

The biological sample utilized for detection can be any body sample such as blood (serum or plasma), sputum, ascites fluids, pleural effusions, urine, biopsy specimens, isolated cells and/or cell membrane preparation. Methods of obtaining tissue biopsies and body fluids from mammals are well known in the art.

The peptide of the present invention is contacted with the biological sample under conditions suitable for aggregate formation (i.e., buffer, temperature, incubation time etc.); suitable conditions are described in Example 2 of the Examples section. Measures are taken not to allow pre-aggregation of peptides prior to incubation with the biological sample. To this end freshly prepared peptide stocks are preferably used.

Protein complexes within a biological sample can be detected via any one of several methods known in the art, which methods can employ biochemical and/or optical detection schemes.

To facilitate complex detection, the peptides of the present invention are highlighted preferably by a tag or an antibody. It will be appreciated that highlighting can be effected prior to, concomitant with or following aggregate formation, depending on the highlighting method. As used herein the term "tag" refers to a molecule, which exhibits a quantifiable activity or characteristic. A tag can be a fluorescent molecule including chemical fluorescers such as fluorescein or polypeptide fluorescers such as the green fluorescent protein (GFP) or related proteins (www.clontech.com). In such case, the tag can be quantified via its fluorescence, which is generated upon the application of a suitable excitatory light. Alternatively, a tag can be an epitope tag, a fairly unique polypeptide sequence to which a specific antibody can bind without substantially cross reacting with other cellular epitopes. Such epitope tags include a Myc tag, a Flag tag, a His tag, a leucine tag, an IgG tag, a streptavidin tag and the like.

Alternatively, aggregate detection can be effected by an antibody designed and configured to specifically react with the peptides of the present invention.

For example, for an antibody specifically recognizing the peptides of the present invention one may use the amino acid sequence epitope of SEQ ID NO:13. Antibodies may be generated via any one of several methods known in the art, which methods can employ induction of in vivo production of antibody molecules, screening immunoglobulin libraries or panels of highly specific binding reagents as disclosed [Orlandi D. R. et al. (1989) Proc. Natl. Acad. Sci. 86:3833-3837, Winter G. et al. (1991) Nature 349:293-299] or generation of monoclonal antibody molecules by continuous cell lines in culture. These include but are not limited to, the hybridoma technique, the human B-cell hybridoma technique, and the Epstein-Bar-Virus (EBV)-hybridoma technique [Kohler G., et al. (1975) Nature 256:495-497, Kozbor D., et al. (1985) J. Immunol. Methods 81:31-42, Cote R. J. et al. (1983) Proc. Natl. Acad. Sci. 80:2026-2030, Cole S. P. et al. (1984) Mol. Cell. Biol. 62:109-120].

Antibody fragments may also be generated. For example, such fragments include F(ab')2 fragments which may be produced by pepsin digestion of the antibody molecule and the Fab fragments which can be generated by reducing the disulfide bridges of the F(ab')2 fragments. Alternatively, Fab expression libraries may be constructed to allow rapid and easy identification of monoclonal Fab fragments with the desired specificity [Huse W. D. et al. (1989) Science 254: 1275-1281].

Thus, this aspect of the present invention provides a method of assaying or screening biological samples, such as body tissue or fluid suspected of including an amyloid fibril.

It will be appreciated that such a detection method can also be utilized in an assay for uncovering potential drugs useful in prevention or disaggregation of amyloid deposits. For example, the present invention may be used for high throughput screening of test compounds. Typically, the co-aggregating peptides of the present invention are radiolabeled, to reduce assay volume. A competition assay is then effected by monitoring displacement of the label by a test compound [Han (1996) J. Am. Chem. Soc. 118:4506-7 and Esler (1996) Chem. 271:8545-8].

It will be appreciated that the peptides of the present invention may also be used as potent detectors of amyloid deposits in-vivo. A designed peptides capable of binding amyloid deposits, labeled non-radioactively or with a radio-isotope, as is well known in the art can be administered to an individual to diagnose the onset or presence of amyloid-related disease, discussed hereinabove. The binding of such a labeled peptide after administration to amyloid or amyloid-like deposits can be detected by in vivo imaging techniques known in the art.

The peptides of the present invention can be included in a diagnostic or therapeutic kit. For example, peptide sets of specific disease related proteins or antibodies directed thereagainst can be packaged in a one or more containers with appropriate buffers and preservatives and used for diagnosis or for directing therapeutic treatment.

Thus, the peptides can be each mixed in a single container or placed in individual containers. Preferably, the containers include a label. Suitable containers include, for example, bottles, vials, syringes, and test tubes. The containers may be formed from a variety of materials such as glass or plastic.

In addition, other additives such as stabilizers, buffers, blockers and the like may also be added.

The peptides of such kits can also be attached to a solid support, such as beads, array substrate (e.g., chips) and the like and used for diagnostic purposes.

Peptides included in kits or immobilized to substrates may be conjugated to a detectable label such as described hereinabove.

The kit can also include instructions for determining if the tested subject is suffering from, or is at risk of developing, a condition, disorder, or disease associated with amyloid polypeptide of interest.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683, 202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Alanine Scan of the hIAPP Basic Amyloidogenic Unit

Rational and Peptide Synthesis

Pancreatic amyloid is found in more than 95% of type II diabetes patients. Pancreatic amyloid is formed by the aggregation of a 37 amino acid long islet amyloid polypeptide (IAPP), the cytotoxicity hereof being directly associated with the development of the disease. IAPP amyloid formation follows a nucleation-dependent polymerization process, which proceeds through conformational transition of soluble IAPP into aggregated β-sheets. Recently it has been shown that a hexapeptide (22-27) (NFGAIL, SEQ ID NO: 14) of IAPP, also termed as the "basic amyloidogenic unit" is sufficient for the formation of β-sheet-containing amyloid fibrils [Konstantinos et al. (2000) J. Mol. Biol. 295:1055-1071].

To gain further insight into the specific role of the residues that compose "the "basic amyloidogenic unit", a systematic alanine scan was performed. Amino-acids were replaced with alanine in order to specifically change the molecular interface of the peptides, without significantly changing their hydrophobicity or tendency to form β-sheet structures. alanine-scan was preformed in the context of the block that is unique to human IAPP (FIG. 1a). This block includes two serine residues that follow the NFGAIL motif in the full-length polypeptide. These eight amino-acid peptide sequences were used since the shorter peptides are hydrophobic and as such less soluble. FIG. 1b shows a schematic representation of the chemical structure of the wild-type peptide while FIG. 1c indicates the amino-acid substitutions in the different mutant peptides that were generated.

Methods and Reagents—

Peptide synthesis was performed by PeptidoGenic Research & Co. Inc (Livermore, Calif. USA). The sequence identity of the peptides was confirmed by ion spray mass-spectrometry using a Perkin Elmer Sciex API I spectrometer. The purity of the peptides was confirmed by reverse phase high-pressure liquid chromatography (RP-HPLC) on a $C_{18}$ column, using a linear gradient of 10 to 70% acetonitrile in water and 0.1% trifluoroacetic acid (TFA).

Example 2

Kinetics of Aggregation of IAPP Peptide Fragment and Mutant Derivatives as Monitored by Turbidity Measurements To study self-assembly of the IAPP peptide derived fragments, aggregation and insolubilization kinetics were monitored using turbidity measurements at 405 nm.

Kinetic Aggregation Assay—

Fresh peptide stock solutions were prepared by dissolving lyophilized form of the peptides in DMSO, a disaggregating solvent, at a concentration of 100 mM. To avoid any pre-aggregation, fresh stock solutions were prepared prior to each and every experiment. Peptide stock solutions were diluted into assay buffer and plated in 96-well plates as follows: 2 μl of peptides stock solutions were added to 98 μl of 10 mM Tris pH 7.2, resulting in a 2 mM final concentration of the peptide in the presence of 2% DMSO. Turbidity data was measured at 405 nm. A buffer solution including 2% DMSO was used as a blank. Turbidity was measured at room temperature over several time points.

Results—

Figure 2:
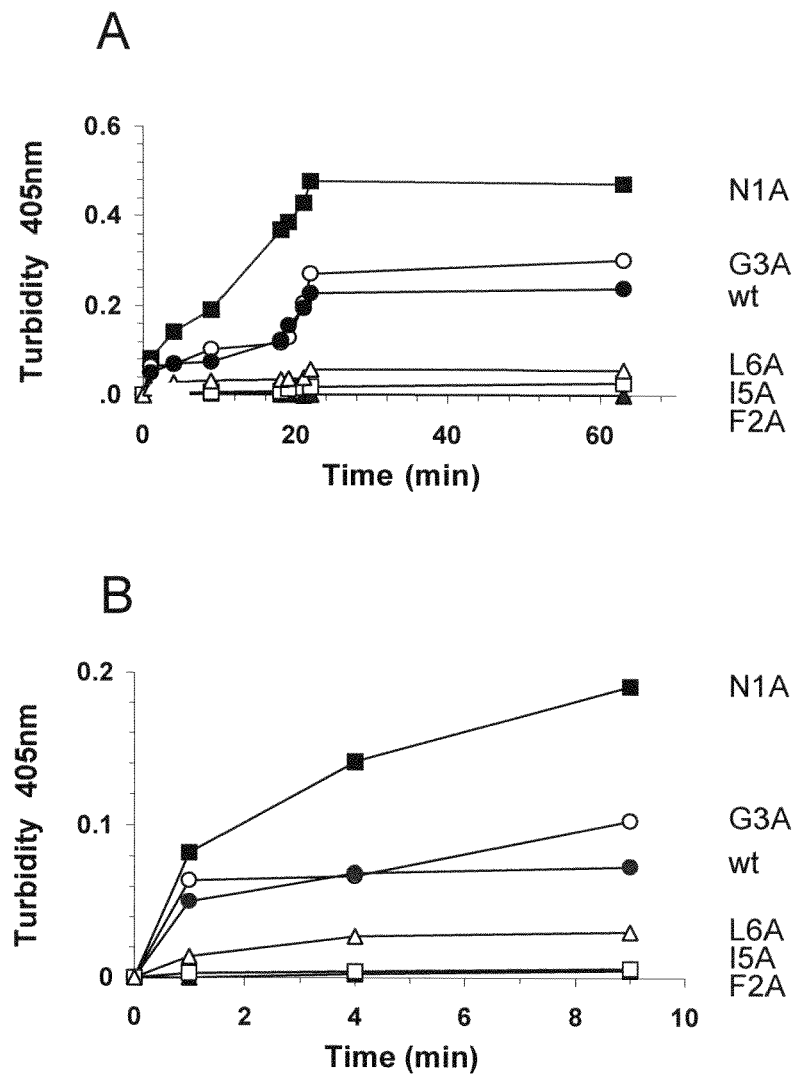
FIGS. 2a-b are graphs illustrating light absorbance at 405 nm as a function of time during fibril formation thus reflecting the aggregation kinetics of the peptides of the present invention. The following symbols are used: closed squares—N1A, opened circles—G3A, closed circles—wild type, opened triangles—L6A, opened squares—I5A and closed triangles—F2A.

As shown in FIG. 2a, wild-type peptide fragment (SEQ ID NO: 1) showed an aggregation kinetic profile that was very similar to those previously reported for non-seeded hIAPP hexapeptide [Tenidis et al. (2000) J. Mol. Biol 295:1055-71]. Such a profile is strongly indicative of a nucleation-dependent polymerization mechanism [Jarrett and Lansbury (1992) Biochemistry 31:6865-70]. Following a lag-time of 20 minutes, wild type peptide self-assembled into insoluble fibrils. Peptide G3A (SEQ ID NO: 4) showed essentially the same profile as that of wild type peptide. The N1A peptide (SEQ ID NO: 2) mediated higher kinetics of aggregation, albeit with different kinetic profile as compared to that of wild-type peptide. Interestingly, the aggregation of N1A seemed to be less nucleation-dependent. Substitution of the isoleucine or leucine to alanine (peptides I5A, SEQ ID NO: 5 and L6A, SEQ ID NO: 6 respectively) reduced the kinetics of aggregation but did not abolish it completely. Substitution of the phenylalanine residue to alanine (peptide F2A, SEQ ID NO:3) led to a total loss of peptide ability to aggregate. The F2A peptide was completely soluble in the aqueous assay buffer.

Altogether, kinetic aggregation studies of the amyloidogenic fragments suggested a major role to the phenylalanine residue in the process of amyloid formation by the IAPP active fragment.

Example 3

Measurement of Aggregate Mean Particle Size

While the turbidity assay provided an important estimate regarding the aggregation potential and kinetics of the various peptides, it did not provide information about the size of the actual aggregates formed. It will be appreciated that although the apparent hydrodynamic diameter of amyloid structures varies due to irregularity of the amyloid structure, it may still provide a clear indication about the order of magnitude of the structure formed and present a quantitative criterion for comparing the structures formed by the various peptides.

Therefore, the average size of the aggregates, formed by the various peptides, was determined using dynamic light scattering (DLS) experiments.

Method—

Freshly prepared peptide stock solutions at a concentration of 10 mM were diluted in 10 mM Tris buffer pH 7.2 and further filtrated through a 0.2 µm filter to a final concentration of 100 µM peptide and 1% DMSO. Particle size measurement was conducted with a laser-powered ALV-NIBS/HPPS non-invasive backscattering instrument. Autocorrelation data was fitted using the ALV-NIBS/HPPS software to derive average apparent hydrodynamic diameters.

Results—

Figure 3:
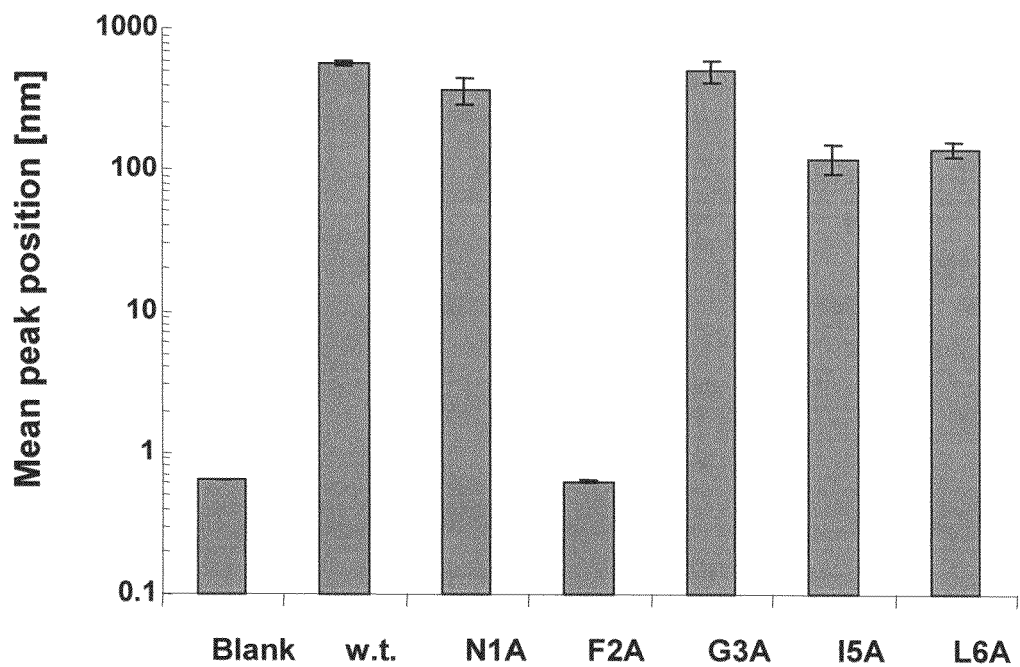
FIG. 3 is a histogram depicting mean particle size of assembled IAPP peptide and derivatives as measured by light scattering. Each column represents the results of 3-5 independent measurements.

The average apparent hydrodynamic diameters of the structures that were formed by the various peptides are presented in FIG. 3.

Altogether, the apparent hydrodynamic diameter of the structures formed by the various peptides seemed to be consistent with the results obtained by the turbidity assay. As with the turbidity assay, the wild-type peptide and G3A peptide formed particles of very similar hydrodynamic diameters. Smaller structures were observed with the derivative peptides: N1A, I5A and L6A. Thus, in accordance with the turbidity assay, the DLS experiments clearly illustrate that no large particles were formed by the F2A peptide under the indicated experimental conditions.

Example 4

Examination of Amyloidogenic Performance of Wild Type Peptide and Derivatives Through Congo Red (CR) Binding Assay Congo red (CR) staining combined with polarization microscopy was utilized to test amyloidogenicity of the peptides of the present invention. Amyloid fibrils in general, and fibrilar IAPP in particular, bind CR and exhibit gold/green birefringence under polarized light [Cooper (1974) Lab. Invest. 31:232-8; Lansbury (1992) Biochemistry 31:6865-70].

Method and Reagents—

Peptide solutions incubated in a 10 mM Tris buffer (pH 7) for four days were dried on a glass microscope slide. Staining was effected by the addition of 1 mM CR in 10 mM Tris buffer pH 7.2 followed by a 1 minute incubation. To remove excess CR, slides were rinsed with double-distilled water and dried. Saturated CR solutions solubilized in 80% ethanol (v/v) were used for poorly aggregating peptides. In such cases, staining was effected without rinsing. Birefringence was determined using a WILD Makroskop m420 (×70) equipped with a polarizing stage.

Results—

Figure 4:
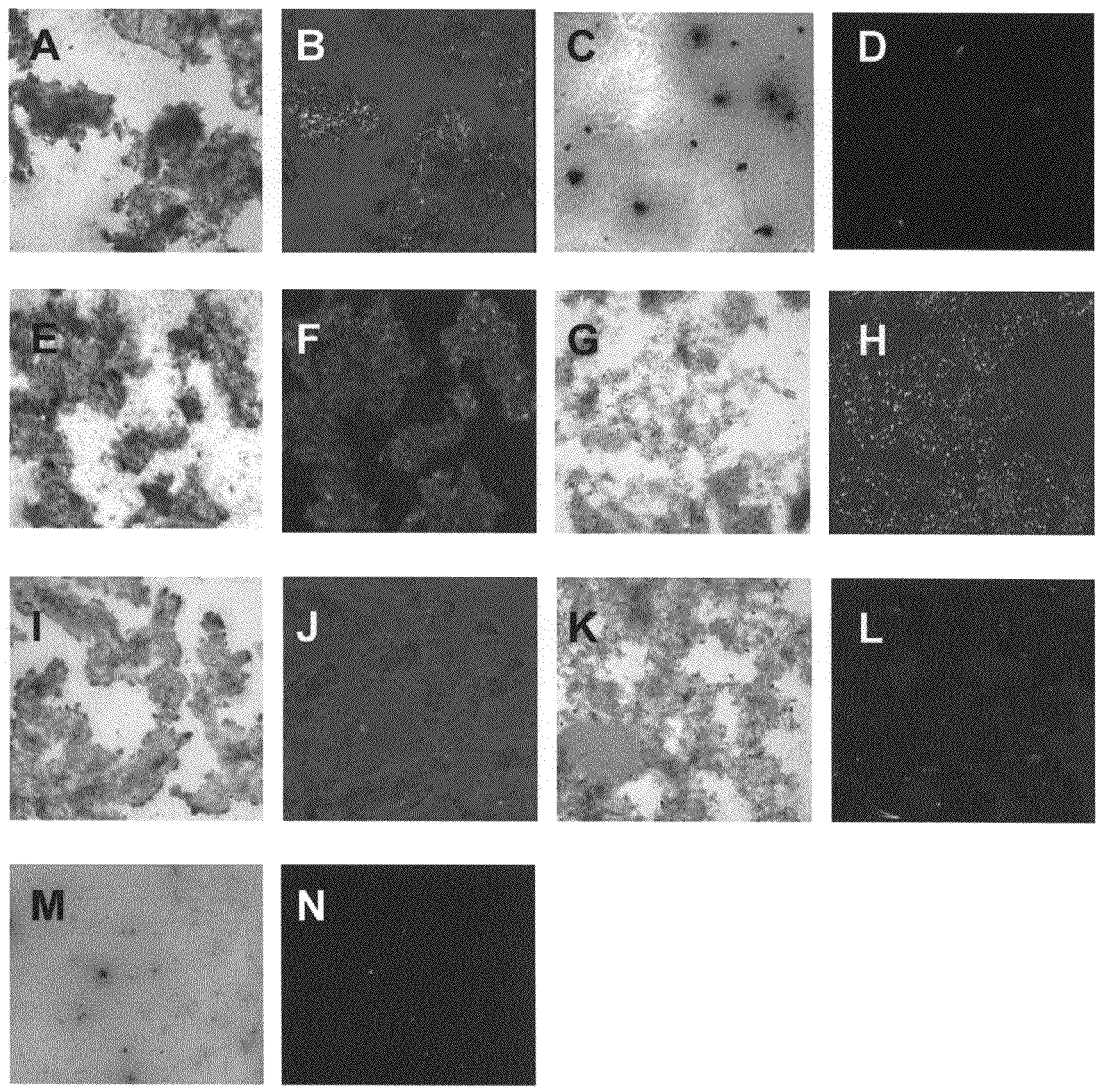
FIGS. 4a-n are photomicrographs illustrating Congo Red binding to pre-assembled IAPP peptides. Normal field and polarized field micrographs are shown respectively for each of the following aged peptide suspensions: N1A peptide (FIGS. 4a-b), F2A peptide (FIGS. 4c-d), G3A peptide (FIGS. 4e-f), wild type peptide (FIGS. 4g-h), I5A peptide (FIGS. 4i-j) and L6A (FIGS. 4k-l).

Wild type, N1A and G3A peptides bound CR and exhibited the characteristic green/gold birefringence (see FIGS. 4g, 4a and 4e for normal field and FIGS. 4h, 4b and 4f for polarized light microscopy, respectively). Peptides I5A and L6A, bound CR and exhibited rare but characteristic birefringence (FIGS. 4i and 4k for normal field and FIGS. 4j and 4l for polarized light, respectively). Peptide F2A (NAGAIL) showed no capability of binding CR (FIG. 4c for normal field and FIG. 4d for polarized light). Dried buffer solution stained with CR was used as a negative control (see FIGS. 4m and 4n for normal and polarized light, respectively). Interestingly, no significant difference in binding was observed for the negative control and the F2A peptide.

To substantiate the inability of F2A peptide to form fibrils, a peptide solution incubated for 14 days was used in the binding assay. Although some degree of aggregation was visually observed following two weeks of peptide "aging", CR staining showed no amyloid structure (results not shown). Under the same conditions wild-type peptide incubation resulted in significant CR birefringence.

Example 5

Ultrastructural Analysis of the Fibrillogenic Peptide and Mutants

The fibrillogenic potential of the various peptides was assessed by electron microscopy analysis.

Method—

Peptide solutions (2 mM peptide in 10 mM Tris buffer pH 7.2), were incubated overnight at room temperature. Fibrils formation was assessed using 10 µl sample placed on 200-mesh copper grids, covered with carbon-stabilized formvar film (SPI Supplies, West Chester Pa.). Following 20-30 seconds of incubation, excess fluid was removed and the grids were negatively stained with 2% uranyl acetate in water. Samples were viewed in a JEOL 1200EX electron microscope operating at 80 kV.

Results—

Figure 5:
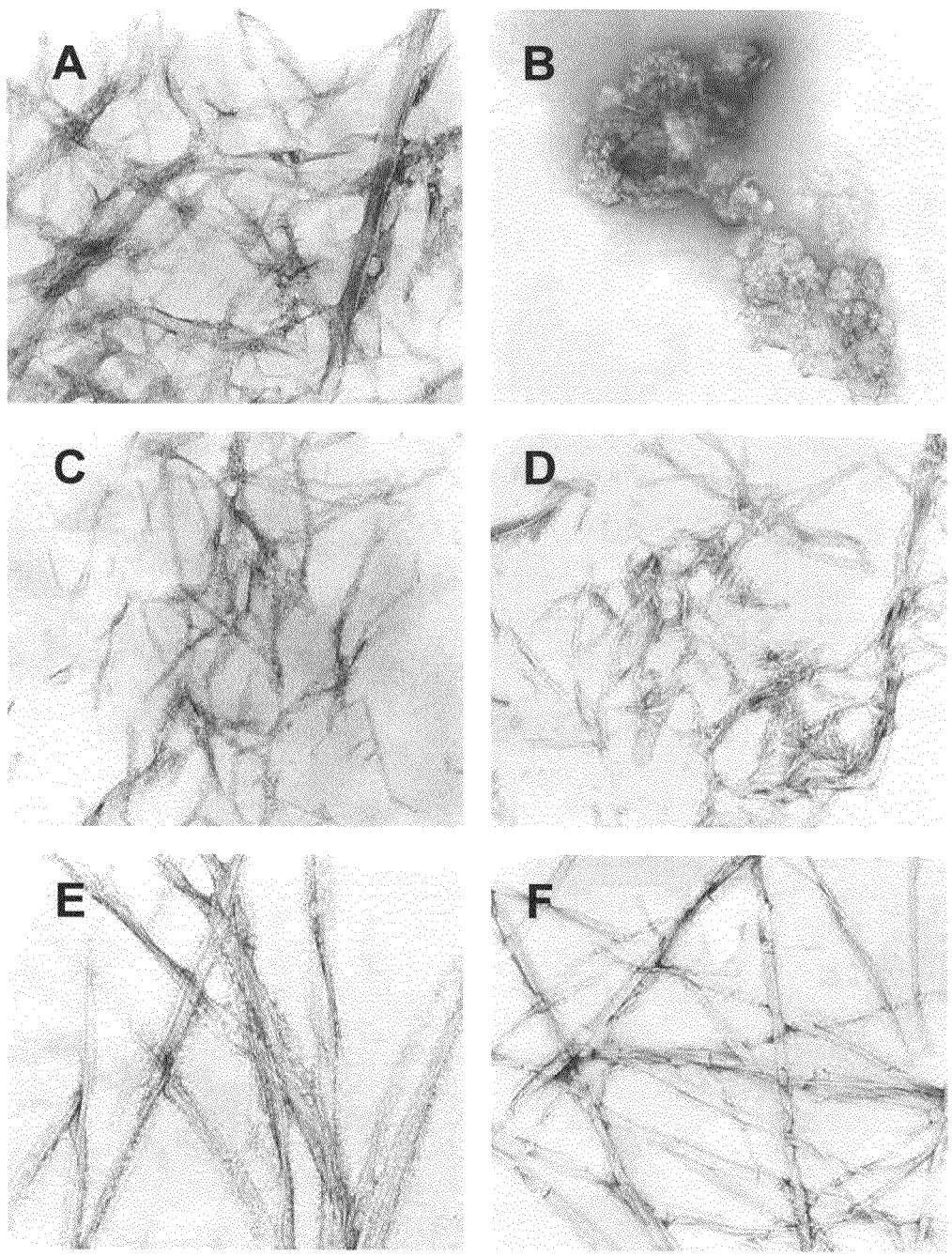
FIGS. 5a-f are electron micrographs of "aged" IAPP peptide and derivatives. N1A peptide (FIG. 5a), F2A peptide (FIG. 5b), G3A peptide (FIG. 5c), wild type peptide (FIG. 5d), I5A peptide (FIG. 5e) and L6A (FIG. 5f). The indicated scale bar represents 100 nm.

To further characterize the structures formed by the various peptides, negative staining electron microscopy analysis was effected. In accordance with previous results, filamentous structures were observed for all peptides (FIGS. 5a-f) but F2A which generated amorphous fibrils (FIG. 5b). Frequency of appearance of fibrils formed by the I5A and L6A peptides (FIGS. 5e and 5f, respectively) was lower in comparison to that of wild type (FIG. 5d), N1A, and G3A peptides (FIGS. 5a and 5c, respectively). Although the EM fields shown for peptides F2A, I5A and L6A, were rarely observed, the results presented by these images support the quantitative results presented in the previous sections and thus provide qualitative analysis of fibril morphology.

The tangled net-like structures that were observed for the wild-type, N1A, and G3A peptides could be explained by the fast kinetics of formation of these fibrils (see Example 2). More distinct structures and longer fibrils, albeit less frequent, were observed with peptides I5A and L6A. These longer fibrils may be a result of a slower kinetics, which allow for a more ordered fibril organization.

Taken together, the qualitative results of the electron microscopy and CR analyses strongly suggest that the phenylalanine residue in the hexaamyloid peptide is crucial for its amyloidogenic potential.

Example 6

Amyloid-Related Proteins Share an Aromatic Consensus Sequence

To substantiate the critical role of the aromatic residue in IAPP assembly and to expand it to other amyloid-related proteins, a homology search was conducted. Homology analysis indicated that the aromatic sequence characteristic is prevalent in numerous other amyloid-related proteins as shown in Table 3, below.

TABLE 3

| Amyloid-related protein | Pathological/physiological condition | Active sequence | Reference |
|---|---|---|---|
| Islet amyloid polypeptide | Type II Diabetes mellitus | FGAIL<br>SEQ ID NO: 15 | Tenidis et al J Mol Biol (2000) 295: 1055-71<br>This study |
| beta-amyloid peptide | Alzheimer's disease | QKLVFF<br>SEQ ID NO: 16<br>LVFFA<br>SEQ ID NO: 17<br>LPFFD<br>SEQ ID NO: 18 | Tjenberg J Biol Chem (1996) 271: 8545-8<br>Findeis Biochemistry (1999) 38: 6791-80<br>Pallitto Biochemistry (1999) 38: 3570-8<br>Soto Nat Med (1998) 4: 822-26 |
| Lactadherin | Aortic medical amyloid | NFGSVQFV*<br>SEQ ID NO: 19 | Haggvist Proc Natl Acad Sci USA (1999) 96: 8669-74 |
| Gelsolin | Finnish hereditary amyloidosis | SFNNGDCCFILD*<br>SEQ ID NO: 20 | Maury Biophys Res Commun (1992) 183: 227-31 |
| Serum amyloid A | Chronic inflammation amyloidosis | SFFSFLGEAFD*<br>SEQ ID NO: 21 | Westermark Biochem Biophys Res Commun 182 27-33 |
| PrP | Creutzfeldt-Jakob disease (CJD) | PHGGGWGQ<br>SEQ ID NO: 22 | Priola J Biol Chem (1998) 11980-5<br>Prusiner Cell (1998) 93: 337-48 |
| $^{35}$p | Yeast prion protein | PQGGYQQYN*<br>SEQ ID NO: 23 | Patino Science (1996) 273: 622-6<br>Tuite Cell (2000) 100: 289-92 |

Aromatic residues are underlined. An asterisk indicates that the minimal active fragment may be shorter.

The significance of aromatic residues in molecular recognition and self-assembly is consistent with the role of π-stacking interactions in chemistry. It is suggested that π-stacking contributes to the enthalpic change (ΔH) in free energy interaction (ΔG). Furthermore π-stacking has an entropic role. Accordingly, ordered water molecules are being released from the aromatic ring by hydrophobic interactions. In line with this, it is suggested that aromatic interactions may significantly reduce the energetic barrier for amyloid formation, thereby accelerating the amyloidosis process. Acceleration in amyloidosis may be accomplished by the geometrically restricted assembly of and high affinity between aromatic moieties. As amyloid fibrils formation is basically a process of molecular recognition and self-assembly, stacking interactions between aromatic residues can provide both an energetic contribution as well as directionality and orientation that is provided by the restricted geometry of planar aromatic rings stacking.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents, and patent applications mentioned in this specification are herein incorporated in their entirety by reference into the specification, to the same extent as if each individual publication, patent, or patent application was specifically and individually indicated to be incorporated herein by reference. In addition, citation or identification of any reference in this application shall not be construed as an admission that such reference is available as prior art to the present invention.

What is claimed is:

1. A method of screening for and identifying compounds that disaggregate amyloid aggregates, the method comprising:
   (a) contacting test compounds to be screened, with an amyloid aggregate formed by causing self-aggregation of a labeled peptide having at least 5 amino acid residues and less than 15 amino acid residues, said peptide comprising an amino acid sequence as set forth in SEQ ID NO: 7 that is capable of self-aggregating into an amyloid aggregate; and
   (b) monitoring displacement of said labeled peptide from the amyloid aggregate by each test compound; and
   (c) identifying any compound shown in said monitoring step to cause displacement of said labeled peptide, thereby causing disaggregation of the amyloid aggregate.

2. The method of claim 1, wherein said peptide further comprises at least two serine residues attached to a C-terminus thereof.

3. The method of claim 1, wherein said peptide is a linear peptide.

4. The method of claim 1, wherein said peptide is a cyclic peptide.

5. The method of claim 1, wherein said sequence as set forth in SEQ ID NO: 7 is the sequence of SEQ ID NO:13.

6. The method of claim 1, wherein said sequence as set forth in SEQ ID NO: 7 is the sequence of SEQ ID NO:4.

7. The method of claim 1, wherein said sequence as set forth in SEQ ID NO: 7 is the sequence of SEQ ID NO:12.

* * * * *

SEQUENCE LISTING

```
<160> NUMBER OF SEQ ID NOS: 23

<210> SEQ ID NO 1
<211> LENGTH: 8
<212> TYPE: PRT
<213> ORGANISM: Artificial sequence
<220> FEATURE:
<223> OTHER INFORMATION: Synthetic peptide

<400> SEQUENCE: 1

Asn Phe Gly Ala Ile Leu Ser Ser
1               5

<210> SEQ ID NO 2
<211> LENGTH: 8
<212> TYPE: PRT
<213> ORGANISM: Artificial sequence
<220> FEATURE:
<223> OTHER INFORMATION: Synthetic peptide
```

```
<400> SEQUENCE: 2

Ala Phe Gly Ala Ile Leu Ser Ser
1               5

<210> SEQ ID NO 3
<211> LENGTH: 8
<212> TYPE: PRT
<213> ORGANISM: Artificial sequence
<220> FEATURE:
<223> OTHER INFORMATION: Synthetic peptide

<400> SEQUENCE: 3

Asn Ala Gly Ala Ile Leu Ser Ser
1               5

<210> SEQ ID NO 4
<211> LENGTH: 8
<212> TYPE: PRT
<213> ORGANISM: Artificial sequence
<220> FEATURE:
<223> OTHER INFORMATION: Synthetic peptide

<400> SEQUENCE: 4

Asn Phe Ala Ala Ile Leu Ser Ser
1               5

<210> SEQ ID NO 5
<211> LENGTH: 8
<212> TYPE: PRT
<213> ORGANISM: Artificial sequence
<220> FEATURE:
<223> OTHER INFORMATION: Synthetic peptide

<400> SEQUENCE: 5

Asn Phe Gly Ala Ala Leu Ser Ser
1               5

<210> SEQ ID NO 6
<211> LENGTH: 8
<212> TYPE: PRT
<213> ORGANISM: Artificial sequence
<220> FEATURE:
<223> OTHER INFORMATION: Synthetic peptide

<400> SEQUENCE: 6

Asn Phe Gly Ala Ile Ala Ser Ser
1               5

<210> SEQ ID NO 7
<211> LENGTH: 5
<212> TYPE: PRT
<213> ORGANISM: Artificial sequence
<220> FEATURE:
<223> OTHER INFORMATION: consensus sequence
<220> FEATURE:
<221> NAME/KEY: misc_feature
<222> LOCATION: (1)..(1)
<223> OTHER INFORMATION: Aromatic amino acid
<220> FEATURE:
<221> NAME/KEY: misc_feature
<222> LOCATION: (2)..(2)
<223> OTHER INFORMATION: Non glycine
<220> FEATURE:
<221> NAME/KEY: misc_feature
<222> LOCATION: (3)..(5)
<223> OTHER INFORMATION: any amino acid

<400> SEQUENCE: 7
```

```
Xaa Xaa Xaa Xaa Xaa
1               5

<210> SEQ ID NO 8
<211> LENGTH: 6
<212> TYPE: PRT
<213> ORGANISM: Artificial sequence
<220> FEATURE:
<223> OTHER INFORMATION: Synthetic peptide

<400> SEQUENCE: 8

Ala Phe Gly Ala Ile Leu
1               5

<210> SEQ ID NO 9
<211> LENGTH: 6
<212> TYPE: PRT
<213> ORGANISM: Artificial sequence
<220> FEATURE:
<223> OTHER INFORMATION: Synthetic peptide

<400> SEQUENCE: 9

Asn Ala Gly Ala Ile Leu
1               5

<210> SEQ ID NO 10
<211> LENGTH: 6
<212> TYPE: PRT
<213> ORGANISM: Artificial sequence
<220> FEATURE:
<223> OTHER INFORMATION: Synthetic peptide

<400> SEQUENCE: 10

Asn Phe Gly Ala Ala Leu
1               5

<210> SEQ ID NO 11
<211> LENGTH: 6
<212> TYPE: PRT
<213> ORGANISM: Artificial sequence
<220> FEATURE:
<223> OTHER INFORMATION: Synthetic peptide

<400> SEQUENCE: 11

Asn Phe Gly Ala Ile Ala
1               5

<210> SEQ ID NO 12
<211> LENGTH: 6
<212> TYPE: PRT
<213> ORGANISM: Artificial sequence
<220> FEATURE:
<223> OTHER INFORMATION: Synthetic peptide

<400> SEQUENCE: 12

Asn Phe Ala Ala Ile Leu
1               5

<210> SEQ ID NO 13
<211> LENGTH: 5
<212> TYPE: PRT
<213> ORGANISM: Artificial sequence
<220> FEATURE:
<223> OTHER INFORMATION: Synthetic peptide

<400> SEQUENCE: 13

Phe Ala Ala Ile Leu
1               5
```

<210> SEQ ID NO 14
<211> LENGTH: 6
<212> TYPE: PRT
<213> ORGANISM: Artificial sequence
<220> FEATURE:
<223> OTHER INFORMATION: Synthetic peptide derived from hIAPP

<400> SEQUENCE: 14

Asn Phe Gly Ala Ile Leu
1               5

<210> SEQ ID NO 15
<211> LENGTH: 5
<212> TYPE: PRT
<213> ORGANISM: Artificial sequence
<220> FEATURE:
<223> OTHER INFORMATION: Islet amyloid polypeptide derived, active site
      sequence

<400> SEQUENCE: 15

Phe Gly Ala Ile Leu
1               5

<210> SEQ ID NO 16
<211> LENGTH: 6
<212> TYPE: PRT
<213> ORGANISM: Artificial sequence
<220> FEATURE:
<223> OTHER INFORMATION: Beta-amyloid peptide derived, active site
      sequence

<400> SEQUENCE: 16

Gln Lys Leu Val Phe Phe
1               5

<210> SEQ ID NO 17
<211> LENGTH: 5
<212> TYPE: PRT
<213> ORGANISM: Artificial sequence
<220> FEATURE:
<223> OTHER INFORMATION: Beta-amyloid peptide derived, active site
      sequence

<400> SEQUENCE: 17

Leu Val Phe Phe Ala
1               5

<210> SEQ ID NO 18
<211> LENGTH: 5
<212> TYPE: PRT
<213> ORGANISM: Artificial sequence
<220> FEATURE:
<223> OTHER INFORMATION: Beta-amyloid peptide derived, active site
      sequence

<400> SEQUENCE: 18

Leu Pro Phe Phe Asp
1               5

<210> SEQ ID NO 19
<211> LENGTH: 8
<212> TYPE: PRT
<213> ORGANISM: Artificial sequence
<220> FEATURE:
<223> OTHER INFORMATION: Lactadherin derived, active site sequence

<400> SEQUENCE: 19

```
-continued

Asn Phe Gly Ser Val Gln Phe Val
1               5

<210> SEQ ID NO 20
<211> LENGTH: 12
<212> TYPE: PRT
<213> ORGANISM: Artificial sequence
<220> FEATURE:
<223> OTHER INFORMATION: Gelsolin derived, active site sequence

<400> SEQUENCE: 20

Ser Phe Asn Asn Gly Asp Cys Cys Phe Ile Leu Asp
1               5                   10

<210> SEQ ID NO 21
<211> LENGTH: 11
<212> TYPE: PRT
<213> ORGANISM: Artificial sequence
<220> FEATURE:
<223> OTHER INFORMATION: Serum amyloid A derived, active site sequence

<400> SEQUENCE: 21

Ser Phe Phe Ser Phe Leu Gly Glu Ala Phe Asp
1               5                   10

<210> SEQ ID NO 22
<211> LENGTH: 8
<212> TYPE: PRT
<213> ORGANISM: Artificial sequence
<220> FEATURE:
<223> OTHER INFORMATION: PrP derived, active site sequence

<400> SEQUENCE: 22

Pro His Gly Gly Gly Trp Gly Gln
1               5

<210> SEQ ID NO 23
<211> LENGTH: 9
<212> TYPE: PRT
<213> ORGANISM: Artificial sequence
<220> FEATURE:
<223> OTHER INFORMATION: 35P - Yeast prion protein derived, active site
      sequence

<400> SEQUENCE: 23

Pro Gln Gly Gly Tyr Gln Gln Tyr Asn
1               5
```